United States Patent
Hallam et al.

(10) Patent No.: US 11,202,768 B2
(45) Date of Patent: Dec. 21, 2021

(54) COMPOSITIONS AND METHODS FOR TREATING AND PREVENTING ADHESIONS AND ILEUS

(71) Applicant: Leading Biosciences, Inc., Carlsbad, CA (US)

(72) Inventors: Thomas Hallam, Solana Beach, CA (US); John Rodenrys, Solana Beach, CA (US)

(73) Assignee: Leading Biosciences, Inc., Carlsbad, CA (US)

(*) Notice: Subject to any disclaimer, the term of this patent is extended or adjusted under 35 U.S.C. 154(b) by 0 days.

(21) Appl. No.: 16/069,121

(22) PCT Filed: Jan. 11, 2017

(86) PCT No.: PCT/US2017/013045
§ 371 (c)(1),
(2) Date: Jul. 10, 2018

(87) PCT Pub. No.: WO2017/123653
PCT Pub. Date: Jul. 20, 2017

(65) Prior Publication Data
US 2019/0117604 A1  Apr. 25, 2019

Related U.S. Application Data

(60) Provisional application No. 62/342,626, filed on May 27, 2016, provisional application No. 62/342,565, (Continued)

(51) Int. Cl.
*A61K 31/195*  (2006.01)
*A61P 41/00*   (2006.01)
(Continued)

(52) U.S. Cl.
CPC .......... *A61K 31/195* (2013.01); *A61K 9/0053* (2013.01); *A61K 9/08* (2013.01);
(Continued)

(58) Field of Classification Search
CPC ...... A61K 31/196; A61K 9/0053; A61K 9/08; A61K 31/195; A61K 31/205; A61P 41/00; A61P 1/00
See application file for complete search history.

(56) References Cited

U.S. PATENT DOCUMENTS 4,171,377 A  10/1979 Green et al.
5,962,405 A  10/1999 Seelich
(Continued)

FOREIGN PATENT DOCUMENTS

CN    102231985 A   11/2011
WO   WO-2006/116626 A2   11/2006
(Continued)

OTHER PUBLICATIONS

Van Bree et al. New therapeutic strategies for postoperative ileus. Nat. Rev. Gastroenterol. Hepatol. 9, 675-683, published online Jul. 17, 2012.*
(Continued)

*Primary Examiner* — Theodore R. Howell
(74) *Attorney, Agent, or Firm* — Kim IP Law Group LLC

(57) ABSTRACT

Disclosed herein are pharmaceutical compositions useful for the treatment and prevention of adhesions and ileus.

20 Claims, 6 Drawing Sheets

Related U.S. Application Data filed on May 27, 2016, provisional application No. 62/308,787, filed on Mar. 15, 2016, provisional application No. 62/308,784, filed on Mar. 15, 2016, provisional application No. 62/277,440, filed on Jan. 11, 2016, provisional application No. 62/277,434, filed on Jan. 11, 2016.

(51) Int. Cl.

| | | |
|---|---|---|
| *A61K 9/08* | (2006.01) | |
| *A61K 47/26* | (2006.01) | |
| *A61K 31/765* | (2006.01) | |
| *A61K 9/00* | (2006.01) | |
| *A61K 31/196* | (2006.01) | |
| *A61K 47/02* | (2006.01) | |
| *A61K 47/10* | (2017.01) | |
| *A61K 33/10* | (2006.01) | |
| *A61K 33/14* | (2006.01) | |
| *A61K 31/7004* | (2006.01) | |
| *A61P 1/00* | (2006.01) | |

(52) U.S. Cl.
CPC .......... *A61K 31/196* (2013.01); *A61K 31/765* (2013.01); *A61K 47/02* (2013.01); *A61K 47/10* (2013.01); *A61K 47/26* (2013.01); *A61P 41/00* (2018.01); *A61K 31/7004* (2013.01); *A61K 33/10* (2013.01); *A61K 33/14* (2013.01); *A61P 1/00* (2018.01)

(56) References Cited

U.S. PATENT DOCUMENTS

| | | | |
|---|---|---|---|
| 6,121,232 A | 9/2000 | Nur et al. | |
| 6,534,283 B1 | 3/2003 | Schmid-Schonbein et al. | |
| 7,276,235 B2 | 10/2007 | Metzner et al. | |
| 8,252,302 B2 | 8/2012 | MacDonald | |
| 8,338,127 B2 | 12/2012 | Rodenrys | |
| 8,541,371 B2 | 9/2013 | Schmid-Schonbein et al. | |
| 8,722,352 B2 | 5/2014 | Rodenrys | |
| 8,957,113 B2 | 2/2015 | Moore et al. | |
| 9,272,034 B2 | 3/2016 | Schmid-Schonbein et al. | |
| 9,278,077 B2 | 3/2016 | DeBrouse | |
| 9,295,715 B2 | 3/2016 | Delano et al. | |
| 9,314,442 B2 | 4/2016 | Hallam et al. | |
| 9,504,736 B2 | 11/2016 | Schmid-Schonbein et al. | |
| 9,775,821 B2 | 10/2017 | Hallam et al. | |
| 9,962,432 B2 | 5/2018 | DeLano et al. | |
| 10,137,100 B2 | 11/2018 | Schmid-Schonbein et al. | |
| 10,772,861 B2 | 9/2020 | Schmid-Schonbein et al. | |
| 2002/0001584 A1 | 1/2002 | Metzner et al. | |
| 2003/0144212 A1 | 7/2003 | Hoffman et al. | |
| 2004/0009917 A1 | 1/2004 | Redl et al. | |
| 2004/0018984 A1 | 1/2004 | Miyazaki | |
| 2007/0299043 A1 | 12/2007 | Hunter et al. | |
| 2010/0179091 A1 | 7/2010 | Schmid-Schonbein et al. | |
| 2011/0060040 A1 | 3/2011 | Virsik et al. | |
| 2013/0046275 A1 | 2/2013 | Holzer et al. | |
| 2013/0310325 A1 | 11/2013 | Schmid-Schonbein et al. | |
| 2014/0018293 A1 | 1/2014 | Delano et al. | |
| 2015/0132360 A1 | 5/2015 | Vickers | |
| 2015/0272914 A1 | 10/2015 | Hallam et al. | |
| 2015/0290157 A1 | 10/2015 | Moore et al. | |
| 2015/0297619 A1 | 10/2015 | Schmid-Schonbein et al. | |

FOREIGN PATENT DOCUMENTS

| | | |
|---|---|---|
| WO | WO-2010/064806 A2 | 6/2010 |
| WO | WO-2010/064806 A3 | 6/2010 |
| WO | WO-2006/116626 A3 | 8/2010 |
| WO | WO-2010/087874 A1 | 8/2010 |
| WO | WO-2011/034539 A1 | 3/2011 |
| WO | WO-2012/045083 A2 | 4/2012 |
| WO | WO-2012/048289 A1 | 4/2012 |
| WO | WO-2013/093164 A1 | 6/2013 |
| WO | WO-2015/099083 A1 | 7/2015 |

OTHER PUBLICATIONS

Kehlet et al. Review of postoperative ileus. American Journal of Surgery, 182, Suppl. to Nov. 2001, 3S-10S.*
Chen et al. Oral urografin in postoperative small bowel obstruction. World J. Surg. 23, 1051-1054, 1999.*
European Search Repot dated Aug. 12, 2019, for EP Patent Application No. 17738872.5, 6 pages.
International Search Report dated Apr. 24, 2017, for PCT Application No. PCT/US2017/013045, 7 pages.
Written Opinion dated Apr. 24, 2017, for PCT Application No. PCT/US2017/013045, 50 pages.
Davidson, E.D. et al. (Jul. 1979). "The effects of metoclopramide on postoperative ileus. A randomized double-blind study," *Ann Surg* 190(1):27-30.
Roberts, J.P. et al. (Feb. 1995). "Effect of cisapride on distal colonic motility in the early postoperative period following left colonic anastomosis," *Dis Colon Rectum* 38(2):139-145.
Von Ritter, C. et al. (Mar. 1987). "Cisapride does not reduce postoperative paralytic ileus," *S Afr J Surg* 25(1):19-21.

* cited by examiner

COMPOSITIONS AND METHODS FOR TREATING AND PREVENTING ADHESIONS AND ILEUS

CROSS-REFERENCES TO RELATED APPLICATIONS

This application is the national stage filing under USC 371 of international application PCT/US2017/013045, filed Jan. 11, 2017, which claims the benefit of U.S. Provisional Application No. 62/277,434, filed Jan. 11, 2016, U.S. Provisional Application No. 62/277,440, filed Jan. 11, 2016, U.S. Provisional Application No. 62/308,787, filed Mar. 15, 2016, U.S. Provisional Application No. 62/308,784, filed Mar. 15, 2016, U.S. Provisional Application No. 62/342,565, filed May 27, 2016, and U.S. Provisional Application No. 62/342,626, filed May 27, 2016, each of which are incorporated herein by reference in their entirety and for all purposes.

BACKGROUND

Adhesions are a type of scar tissue which may connect organs and tissues that are not typically connected. They may form as a result from multiple types of trauma or inflammation, such as surgery, wounding, infection, radiation or other disease. Almost any inflamed tissue can form adhesions to adjacent, tissue if these tissues are left in contact over time. It is theorized that within several minutes light adhesions form, and are most frequently replaced after several days by heavy permanent adhesions. It has been estimated that more than 98% of all patients undergoing abdominal surgery develop internal adhesions. Such adhesions also complicate pelvic, thoracic, articular, orthopedic, and neuro surgery. Adhesions are the greatest cause of intestinal obstruction and strangulation. They are also the greatest cause of infertility in females. Once adhesions have formed, medical complications from those adhesions may develop at any point in a patient's lifetime. The initiation of an adhesion begins with the formation of a fibrin matrix, typically occurring from coagulation following trauma or inflammation. When two peritoneal surfaces are in close proximity following an injury, digestive enzymes work to degrade the fibrin matrix and replace it with vascular tissue. Eventually the adhesion matures into a fibrous band often containing mesothelium, blood vessels, and connective tissue fibers. Abdominal adhesions occur after approximately 95% of all abdominal surgeries, with up to 6% of cases requiring follow-up care. Adhesions are also present in 10.4% of individuals who have never had abdominal surgery. In the US each year, 400,000 individuals require surgical correction (lysis of adhesions, or adhesiolysis) of abdominal adhesions. Nearly 30% of patients who undergo lysis of adhesions from small bowel obstruction require yet another operation to lyse recurrent adhesions. Adhesions are difficult to treat and prevent.

Ileus is a partial or complete non-mechanical obstruction of the small and/or large intestine and occurs when peristalsis, the rhythmic contraction that moves material through the bowel, stops. Ileus can be caused, for example, by manipulation of the intestines during abdominal surgery, inflammation of the peritoneum, or administration of narcotics or chemotherapeutic agents. Post-operative ileus is commonly observed following abdominal surgery with intestinal manipulation. The condition is characterized by generalized hypomotility of the gastrointestinal tract and delayed gastric emptying, in the absence of mechanical bowel obstruction, leading to increased morbidity and prolonged hospitalization. Intestinal handling results in impaired contractility and delayed transit in the gastrointestinal tract, resulting in accumulation of gas and fluids within the bowel. Post-operative ileus frequently occurs after intraperitoneal surgery, but it may also occur after retroperitoneal and extra-abdominal surgery. The longest duration of post-operative ileus is noted to occur after colonic surgery. The clinical consequences of post-operative ileus can be profound. Patients with post-operative ileus are immobilized, have discomfort and pain, and are at increased risk for pulmonary complications. Furthermore, post-operative ileus may result in delayed hospital release and hospital readmissions. For many, if not most, patients undergoing surgery (e.g., abdominal or gastrointestinal surgery), return of bowel function is the factor that delays going home; patients remain in the hospital until post-operative ileus has resolved and gastrointestinal function has returned to normal. Additionally, post-operative ileus may be a significant contributing factor for hospital readmissions. A retrospective review of more than 800,000 patients who underwent surgery in the United States in 2002 found a 4.25% rate of postoperative ileus. The hospital length of stay was 9.3 days in patients with post-operative ileus compared to only 5.3 days in those without it, and the difference in total hospital costs was US $6,300 per patient. Johnson et al, Cleveland Clinic Journal of Medicine, 76(11):641-648 (2009). The costs become very significant when you consider the number of surgical procedures performed every year. Currently, there are no broadly effective treatments for ileus, including post-operative ileus, and interventions generally rely on supportive measures.

The disclosure is directed to new pharmaceutical compositions that are useful in preventing and treating adhesions or ileus. Disclosed herein, inter alia, are solutions to these and other problems in the art.

BRIEF SUMMARY OF THE INVENTION

The disclosure provides methods for treating or preventing adhesions or ileus in a patient in need thereof by administering to the patient a therapeutically effective amount of an aqueous pharmaceutical composition including tranexamic acid. The disclosure provides methods for treating or preventing adhesions or ileus in a patient in need thereof by administering to the patient a therapeutically effective amount of an aqueous pharmaceutical composition including tranexamic acid, polyethylene glycol, and, optionally, at least one electrolyte. The disclosure provides methods for treating or preventing adhesions or ileus in a patient in need thereof by administering to the patient a therapeutically effective amount of an aqueous pharmaceutical composition including tranexamic acid, glucose, and, optionally, at least one electrolyte. The disclosure provides methods for treating or preventing adhesions or ileus in a patient in need thereof by administering to the patient a therapeutically effective amount of an aqueous pharmaceutical composition including tranexamic acid, polyethylene glycol, glucose, and at least one electrolyte. The methods for treating or preventing adhesions include methods of reducing the incidence of adhesions; methods of reducing the number of adhesions; methods of reducing the severity of adhesions; methods of reducing the thickness of adhesions; methods of preventing the formation of adhesions; or a combination of two or more thereof. The pharmaceutical composition may be administered to the patient orally or by lavage. When administered orally, the pharmaceutical composition is administered prior to a surgical procedure, after a surgical procedure, or before and after a surgical procedure. When administered by lavage during a surgical procedure, the pharmaceutical composition is administered to the peritoneal cavity, the intercostal space, the stomach, the intestines, or a combination of two or more thereof. In embodiments, the pharmaceutical composition is administered orally. In embodiments, the pharmaceutical composition is orally administered to prevent adhesions or ileus. In embodiments, the pharmaceutical composition is orally administered prior to a surgical procedure to prevent adhesions or ileus. Ileus may be postoperative ileus. In embodiments, the methods are to prevent adhesions. In embodiments, the methods are to prevent ileus. In embodiments, the methods are to treat adhesions. In embodiments, the methods are to treat ileus.

The disclosure provides methods for treating or preventing adhesions or ileus in a patient in need thereof by orally administering to the patient a therapeutically effective amount of an aqueous pharmaceutical composition including tranexamic acid, prior to a surgical procedure. The disclosure provides methods for treating or preventing adhesions or ileus in a patient in need thereof by orally administering to the patient a therapeutically effective amount of an aqueous pharmaceutical composition including tranexamic acid, polyethylene glycol, and, optionally, at least one electrolyte, prior to a surgical procedure. The disclosure provides methods for treating or preventing adhesions or ileus in a patient in need thereof by orally administering to the patient a therapeutically effective amount of an aqueous pharmaceutical composition including tranexamic acid, glucose, and, optionally, at least one electrolyte, prior to a surgical procedure. The disclosure provides methods for treating or preventing adhesions or ileus in a patient in need thereof by orally administering to the patient a therapeutically effective amount of an aqueous pharmaceutical composition including tranexamic acid, polyethylene glycol, glucose, and at least one electrolyte, prior to a surgical procedure. The methods for treating or preventing adhesions include methods of reducing the incidence of adhesions; methods of reducing the number of adhesions; methods of reducing the severity of adhesions; methods of reducing the thickness of adhesions; methods of preventing the formation of adhesions; or a combination of two or more thereof. In embodiments, the methods are for preventing adhesions. In embodiments, the methods are for treating adhesions. In embodiments, the methods are for preventing ileus. In embodiments, the methods are for treating ileus. In embodiments, the methods are for reducing the incidence of adhesions. In embodiments, the methods are for reducing the number of adhesions. In embodiments, the methods are for reducing the severity of adhesions. In embodiments, the methods are for reducing the thickness of adhesions. In embodiments, the methods are for preventing the formation of adhesions.

The disclosure provides methods for treating or preventing adhesions or ileus in a patient in need thereof by orally administering to the patient a therapeutically effective amount of an aqueous pharmaceutical composition including tranexamic acid; and subsequently administering to the patient by lavage during a surgical procedure a second aqueous pharmaceutical composition including tranexamic acid, and optionally, one or more compounds selected from the group consisting of polyethylene glycol, glucose, and electrolytes. The disclosure provides methods for treating or preventing adhesions or ileus in a patient in need thereof by orally administering to the patient a therapeutically effective amount of an aqueous pharmaceutical composition including tranexamic acid, polyethylene glycol, and, optionally, at least one electrolyte; and subsequently administering to the patient by lavage during a surgical procedure a second aqueous pharmaceutical composition including tranexamic acid, and optionally, one or more compounds selected from the group consisting of polyethylene glycol, glucose, and electrolytes. The disclosure provides methods for treating or preventing adhesions or ileus in a patient in need thereof by orally administering to the patient a therapeutically effective amount of an aqueous pharmaceutical composition including tranexamic acid, glucose, and, optionally, at least one electrolyte; and subsequently administering to the patient by lavage during a surgical procedure a second aqueous pharmaceutical composition including tranexamic acid, and optionally, one or more compounds selected from the group consisting of polyethylene glycol, glucose, and electrolytes. The disclosure provides methods for treating or preventing adhesions or ileus in a patient in need thereof by orally administering to the patient a therapeutically effective amount of an aqueous pharmaceutical composition including tranexamic acid, polyethylene glycol, glucose, and at least one electrolyte; and subsequently administering to the patient by lavage during a surgical procedure a second aqueous pharmaceutical composition including tranexamic acid, and optionally, one or more compounds selected from the group consisting of polyethylene glycol, glucose, and electrolytes. In embodiments, the second aqueous pharmaceutical composition includes tranexamic acid, polyethylene glycol, glucose, and at least one electrolyte. In embodiments, the second aqueous pharmaceutical composition includes tranexamic acid, polyethylene glycol, and at least one electrolyte. In embodiments, the second aqueous pharmaceutical composition includes tranexamic acid, but does not further include (i) polyethylene glycol, (ii) glucose, or (iii) polyethylene glycol and glucose. In embodiments, the second aqueous pharmaceutical composition is administered by lavage to the peritoneal cavity, the intercostal space, the stomach, the intestines, directly to tissue surfaces, or a combination of two or more thereof. In embodiments, a third aqueous pharmaceutical composition may be orally administered to the patient at any time after completion of the surgical procedure and/or when the patient is in recovery, wherein the third aqueous pharmaceutic composition includes tranexamic acid, polyethylene glycol, glucose, and at least one electrolyte. Alternatively, the third aqueous pharmaceutic composition includes tranexamic acid, and one or more compounds selected from the group consisting polyethylene glycol, glucose, and at least one electrolyte. In embodiments, the methods are to prevent adhesions. In embodiments, the methods are to prevent ileus. In embodiments, the methods are to treat adhesions. In embodiments, the methods are to treat ileus.

The disclosure provides methods to prevent adhesions or ileus by administering a pharmaceutical composition including tranexamic acid. The disclosure provides methods to prevent adhesions or ileus by administering a pharmaceutical composition including tranexamic acid, polyethylene glycol, and, optionally, at least one electrolyte. The disclosure provides methods to prevent adhesions or ileus by administering a pharmaceutical compositions including tranexamic acid, glucose, and, optionally, at least one electrolyte. The disclosure provides methods to prevent adhesions or ileus by administering a pharmaceutical composition including tranexamic acid, polyethylene glycol, glucose, and at least one electrolyte. Ileus may be postoperative ileus. In embodiments, the methods are to prevent adhesions. In embodiments, the methods are to prevent ileus.

The disclosure provides methods to prevent adhesions or ileus by orally administering a pharmaceutical composition including tranexamic acid, prior to a surgical procedure. The disclosure provides methods to prevent adhesions or ileus by orally administering a pharmaceutical composition including tranexamic acid, polyethylene glycol, and, optionally, at least one electrolyte, prior to a surgical procedure. The disclosure provides methods to prevent adhesions or ileus by orally administering a pharmaceutical composition including tranexamic acid, glucose, and, optionally, at least one electrolyte, prior to a surgical procedure. The disclosure provides methods to prevent adhesions or ileus by orally administering a pharmaceutical composition including tranexamic acid, polyethylene glycol, glucose, and at least one electrolyte, prior to a surgical procedure. Ileus may be postoperative ileus. In embodiments, the methods are to prevent adhesions. In embodiments, the methods are to prevent ileus.

The disclosure provides methods to reduce the complications caused by adhesions or ileus by administering a pharmaceutical composition including tranexamic acid. The disclosure provides methods to reduce the complications caused by adhesions or ileus by administering a pharmaceutical composition including tranexamic acid, polyethylene glycol, and, optionally, at least one electrolyte. The disclosure provides methods to reduce the complications caused by adhesions or ileus by administering a pharmaceutical composition including tranexamic acid, glucose, and, optionally, at least one electrolyte. The disclosure provides methods to reduce the complications caused by adhesions or ileus by administering a pharmaceutical composition including tranexamic acid, polyethylene glycol, glucose, and at least one electrolyte. Complications caused by adhesions include, for example, intestinal obstructions, infertility, pain, blood loss, and subsequent surgeries. The pain can be chronic abdominal pain. Exemplary complications caused by ileus include nausea, vomiting, abdominal distention, and the inability to eat, drink, pass flatus, and pass stool. In embodiment, the methods are to reduce the complications cause by adhesions. In embodiments, the methods are to reduce the complications caused by ileus. A complication of ileus and adhesions can be improper bowel functioning or a delayed recovery in bowel functioning.

The disclosure provides methods to reduce the complications caused by adhesions or ileus by orally administering a pharmaceutical composition including tranexamic acid, prior to a surgical procedure. The disclosure provides methods to reduce the complications caused by adhesions or ileus by orally administering a pharmaceutical composition including tranexamic acid, polyethylene glycol, and, optionally, at least one electrolyte, prior to a surgical procedure. The disclosure provides methods to reduce the complications caused by adhesions or ileus by orally administering a pharmaceutical composition including tranexamic acid, glucose, and, optionally, at least one electrolyte, prior to a surgical procedure. The disclosure provides methods to reduce the complications caused by adhesions or ileus by orally administering a pharmaceutical composition including tranexamic acid, polyethylene glycol, glucose, and at least one electrolyte, prior to a surgical procedure. Complications caused by adhesions include, for example, intestinal obstructions, infertility, pain, blood loss, and subsequent surgeries. The pain can be chronic abdominal pain. Exemplary complications caused by ileus include nausea, vomiting, abdominal distention, and the inability to eat, drink, pass flatus, and pass stool. In embodiment, the methods are to reduce the complications cause by adhesions. In embodiments, the methods are to reduce the complications caused by ileus. A complication of ileus and adhesions can be improper bowel functioning or a delayed recovery in bowel functioning.

In embodiments of the methods described herein, the pharmaceutical composition includes about 0.1 wt % to about 2.5 wt % of tranexamic acid, about 2.5 wt % to about 8.0 wt % of polyethylene glycol, and about 0.1 wt % to about 2.5 wt % of at least one electrolyte. In embodiments of the methods described herein, the pharmaceutical composition includes about 0.4 wt % to about 1.8 wt % of tranexamic acid, about 3.9 wt % to about 5.3 wt % of polyethylene glycol, and about 0.6 wt % to about 1.3 wt % of at least one electrolyte. In embodiments of the methods described herein, the pharmaceutical composition includes about 0.7 wt % to about 1.5 wt % of tranexamic acid, about 4.2 wt % to about 5.0 wt % of polyethylene glycol, and about 0.8 wt % to about 1.1 wt % of at least one electrolyte. In embodiments of the methods described herein, the pharmaceutical composition includes about 0.9 wt % to about 1.3 wt % of tranexamic acid, about 4.4 wt % to about 4.8 wt % of polyethylene glycol, and about 0.9 wt % to about 1.0 wt % of at least one electrolyte. In embodiments of the methods described herein, the pharmaceutical composition includes about 1.1 wt % of tranexamic acid, about 4.6 wt % of polyethylene glycol, and about 0.96 wt % of at least one electrolyte. The polyethylene glycol used in the compositions described herein may have an average molecular weight from about 100 Daltons to about 10,000 Daltons; from about 100 Daltons to about 9,000 Daltons; from about 500 Daltons to about 8,000 Daltons; from about 1,000 Daltons to about 6,000 Daltons; from about 2,000 Daltons to about 5,000 Daltons; from about 2,500 Daltons to about 4,500 Daltons; from about 3,000 Daltons to about 4,000 Daltons; from about 3,000 Daltons to about 3,500 Daltons; from about 3,300 Daltons to about 3,400 Daltons; or about 3,500 Daltons. The electrolyte used in the compositions described herein may be sodium, sulfate, bicarbonate, chloride, potassium, or a combination of two or more thereof. In embodiments of the methods described herein, the volume of the aqueous pharmaceutical composition is about 100 mL to about 2,000 mL; about 250 ml to about 1,500 ml; about 300 mL to about 1,000 mL from about 500 mL to about 900 mL; from about 600 mL to about 800 mL; or about 700 mL.

In embodiments of the methods described herein, the pharmaceutical composition includes about 0.05 wt % to about 5.0 wt % of tranexamic acid, about 0.5 wt % to about 15.0 wt % of polyethylene glycol, about 0.01 wt % to about 25.0 wt % of glucose, and about 0.001 wt % to about 10 wt % of at least one electrolyte. In embodiments of the methods described herein, the pharmaceutical composition includes about 0.1 wt % to about 2.5 wt % of tranexamic acid, about 2.5 wt % to about 8.0 wt % of polyethylene glycol, about 0.1 wt % to about 10.0 wt % of glucose, and about 0.1 wt % to about 2.5 wt % of at least one electrolyte. In embodiments of the methods described herein, the pharmaceutical composition includes about 0.4 wt % to about 1.8 wt % of tranexamic acid, about 3.9 wt % to about 5.3 wt % of polyethylene glycol, about 1.0 wt % to about 7.0 wt % of glucose, and about 0.6 wt % to about 1.3 wt % of at least one electrolyte. In embodiments of the methods described herein, the pharmaceutical composition includes about 0.7 wt % to about 1.5 wt % of tranexamic acid, about 4.2 wt % to about 5.0 wt % of polyethylene glycol, about 2.0 wt % to about 6.0 wt % of glucose, and about 0.8 wt % to about 1.1 wt % of at least one electrolyte. In embodiments of the methods described herein, the pharmaceutical composition includes about 0.9 wt % to about 1.3 wt % of tranexamic acid, about 4.4 wt % to about 4.8 wt % of polyethylene glycol, about 3.0 wt % to about 5.0 wt % of glucose, and about 0.9 wt % to about 1.0 wt % of at least one electrolyte. In embodiments of the methods described herein, the pharmaceutical composition includes about 1.1 wt % of tranexamic acid, about 4.6 wt % of polyethylene glycol, about 4.0 wt % of glucose, and about 0.96 wt % of at least one electrolyte. The polyethylene glycol used in the compositions described herein may have an average molecular weight from about 100 Daltons to about 10,000 Daltons; from about 100 Daltons to about 9,000 Daltons; from about 500 Daltons to about 8,000 Daltons; from about 1,000 Daltons to about 6,000 Daltons; from about 2,000 Daltons to about 5,000 Daltons; from about 2,500 Daltons to about 4,500 Daltons; from about 3,000 Daltons to about 4,000 Daltons; from about 3,000 Daltons to about 3,500 Daltons; from about 3,300 Daltons to about 3,400 Daltons; or about 3,500 Daltons. The electrolyte used in the compositions described herein may be sodium, sulfate, bicarbonate, chloride, potassium, or a combination of two or more thereof. In embodiments of the methods described herein, the pharmaceutical composition includes about 1.1 wt % of tranexamic acid, about 4.6 wt % of polyethylene glycol having an average molecular weight of about 3,350, about 4.0 wt % of glucose, about 0.57 wt % of sodium sulfate, about 0.17 wt % of sodium bicarbonate, about 0.15 wt % of sodium chloride, and about 0.07 wt % of potassium chloride. In embodiments of the methods described herein, the volume of the aqueous pharmaceutical composition is about 100 mL to about 2,000 mL; about 300 mL to about 1,000 mL from about 500 mL to about 900 mL; from about 600 mL to about 800 mL; or about 700 mL.

BRIEF DESCRIPTION OF THE DRAWINGS

FIG. 1A shows rat intestines having adhesions, where the intestines were treated with a saline vehicle. FIG. 1B shows rat intestines that do not have any adhesions, where the intestines were treated with Formula A.

FIG. 2 demonstrates that the groups which received enteral Formula A, lavage tranexamic acid (TXA) and saline, and a combination of enteral administration of Formula A with a tranexamic acid (TXA) lavage resulted in significantly less adhesions relative to the control.

FIG. 3 demonstrates that the groups which received enteral Formula A, lavage tranexamic acid (TXA) and saline, and a combination of enteral administration of Formula A with a tranexamic acid (TXA) lavage resulted in significantly smaller adhesions in terms of severity relative to the control.

FIG. 4 demonstrates that the group receiving orally administered Formula A had significantly less adhesions 35 days post-bowel resection surgery compared to the group receiving orally administered placebo.

FIG. 5 demonstrates that the group receiving orally administered Formula A had similar adhesions in terms of severity 35 days post-bowel resection surgery compared to the group receiving orally administered placebo.

DETAILED DESCRIPTION

Figure 1A:
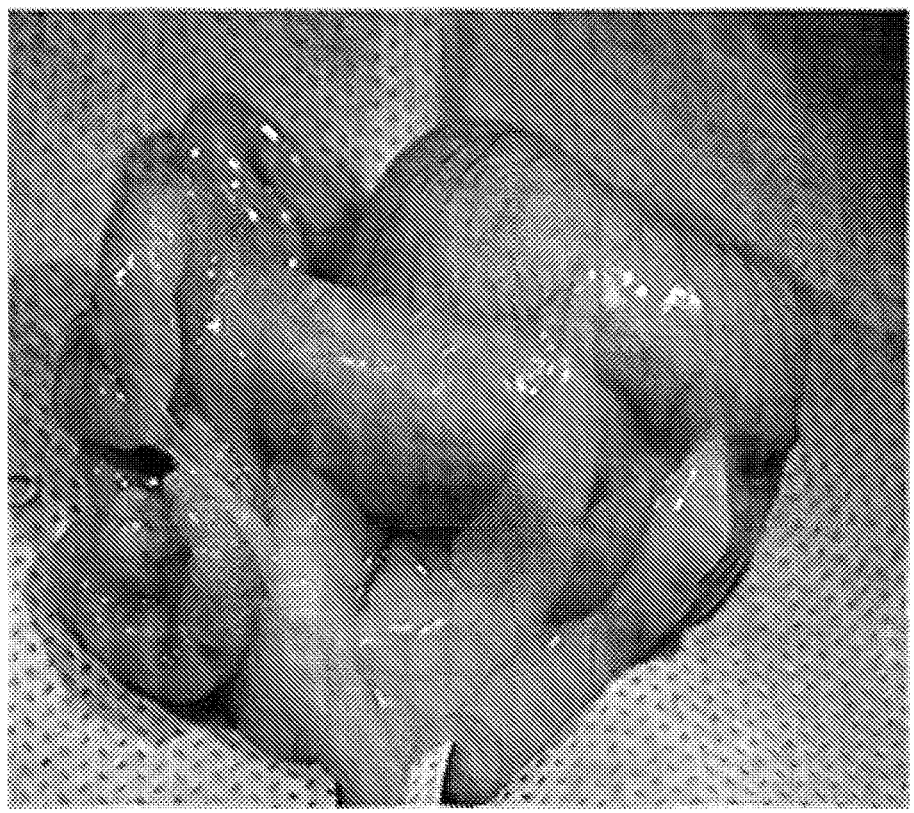
FIGS. 1A-1B.
Figure 1B:

Provided herein are methods to treat and prevent adhesions or ileus by orally administering to a patient prior to a surgical procedure a pharmaceutical composition comprising tranexamic acid. Provided herein are methods to treat and prevent adhesions or ileus by administering to a patient in need a pharmaceutical composition comprising tranexamic acid, where the methods of administration include oral and enteral administration, lavage, or a combination thereof. In embodiments, ileus is postoperative ileus. In embodiments, ileus is paralytic ileus. In embodiments, the methods are to prevent adhesions. In embodiments, the methods are to prevent ileus. In embodiments, the methods are to treat adhesions. In embodiments, the methods are to treat ileus.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

The term "pharmaceutically acceptable salts" is meant to include salts of the active compounds, such as electrolytes, that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts.

The terms "treating" or "treatment" refers to any indicia of success in the treatment or amelioration of adhesions or ileus. For example certain methods herein treat adhesions or ileus by decreasing, reducing, or preventing the occurrence, growth, thickness, number, severity, or progression of adhesions or ileus, or by decreasing, reducing, or preventing a symptom of adhesions or ileus. Symptoms of adhesions would be known or may be determined by a person of ordinary skill in the art. Exemplary symptoms of ileus include nausea, vomiting, abdominal cramps, abdominal bloating, constipation, difficulty tolerating a normal diet, inability to pass gas, and inability to pass stool. Exemplary measurements to identify the effective treatment or prevention of ileus by the pharmaceutical compositions described herein include appetite (as measured by food consumption and/or water consumption), intestinal motility (as measured by fecal production), and body weight. Patients with ileus will have decreased food and water consumption, decreased fecal production, and decreased body weight.

"Treating and preventing adhesions or ileus" and "treating or preventing adhesions or ileus" can include (i) treating adhesions; (ii) preventing adhesions; (iii) treating and preventing adhesions; (iv) treating ileus; (v) preventing ileus; (vi) treating and preventing ileus; (vii) treating adhesions and ileus; (viii) preventing adhesions and ileus; and (ix) treating and preventing adhesions and ileus. In embodiments, the terms mean treating adhesions. In embodiments, the terms mean preventing adhesions. In embodiments, the terms mean treating ileus. In embodiments, the terms mean preventing ileus.

An "effective amount" is an amount sufficient to accomplish a stated purpose (e.g. achieve the effect for which it is administered, treat adhesions, reduce the incidence of adhesions or ileus, reduce the number of adhesions, reduce the severity of adhesions or ileus, reduce the thickness of adhesions or ileus, reduce one or more symptoms of a disease or condition). An example of an "effective amount" is an amount sufficient to contribute to the treatment, prevention, or reduction of a symptom or symptoms of adhesions or ileus, which could also be referred to as a "therapeutically effective amount." A "reduction" of a symptom or symptoms (and grammatical equivalents of this phrase) means decreasing of the severity or frequency of the symptom(s), or elimination of the symptom(s). An "effective amount" of a drug is an amount of a drug that, when administered to a subject, will have the intended effect, e.g., preventing or delaying the onset (or reoccurrence) of an injury, disease, pathology or condition, or reducing the likelihood of the onset (or reoccurrence) of an injury, disease, pathology, or condition, or their symptoms. The full effect does not necessarily occur by administration of one dose, and may occur only after administration of a series of doses. Thus, an effective amount may be administered in one or more administrations. Determination of a therapeutically effective amount of a compound of the invention is within the capabilities of a skilled artisan, particularly in light of the detailed disclosure herein. As is known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards. Adjusting the dose to achieve maximal efficacy in humans based on the methods described herein and other methods is well within the capabilities of the ordinarily skilled artisan.

"Dose" refers to the volume of the pharmaceutical compositions described herein that is administered to the patient, where each of the components (e.g., tranexamic acid) in the pharmaceutical composition are in an amount (e.g., wt %, grams) as described herein.

"Surgical procedure" or "surgery" refers to any surgical procedure known in the art that could directly or indirectly cause adhesions or ileus. In embodiments, the "surgical procedure" involves or is near any internal organ, such as the stomach, intestines, colon, liver, kidney, pancreas, and reproductive organs. In embodiments, the "surgical procedure" is a surgical procedure involving the digestive system, excretory system, reproductive system, skeletal system, nervous system, respiratory system, cardiovascular system, skeletal system, and the like. In embodiments, the "surgical procedure" is a gastrointestinal surgical procedure involving the stomach and/or intestines.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, and other non-mammalian animals. In some embodiments, a patient is human. In some embodiments, a subject is human.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

"Administering" generally means oral administration or administration by lavage. Alternative modes of administration may be possible, such as intravenous, parenteral, intraperitoneal, intramuscular, intralesional, intrathecal, intracranial, intranasal or subcutaneous administration. Liquid form preparations include solutions, suspensions, and emulsions, preferably solutions.

"Oral administration" and "orally administering" refers to ingestion of the pharmaceutical compositions described herein by mouth and into the gastrointestinal tract of the patient. Oral administration may include gavage, where the pharmaceutical compositions described herein are administered to a patient through a tube (e.g., nasogastric) leading down from the throat or nose to the stomach. The term "gavage" is used interchangeably with the term "enteral."

"Molecular weight" or "average molecular weight" refers to number average molecular weight.

"About" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

"Adhesion" or "adhesions" is used in accordance with its plain ordinary meaning in the medical field, and refers to internal scar tissue which extends from one tissue to another tissue. For example an adhesion may form between two different tissues or it may form between two parts of the same tissue at different locations. In embodiments, adhesions are a type of scar tissue which may undesirably form between inflamed or traumatized portions of an organ and adjacent body tissues. The adhesion may be a surgical adhesion. The adhesion may be a peritoneal adhesion. The adhesion may be an abdominal adhesion. The adhesion may be an intercostal adhesion. The adhesion may be caused by surgery, a perforated ulcer, an infection in a fallopian tube, an abdominal trauma, or abdominal radiation treatment.

Adhesions may be further classified relative to which tissues or organs are involved. For example, the formation of scar tissue involving the intestines (e.g., small or large intestine) may be referred to herein as intestinal adhesions. The formation of scar tissue including the inner lining of the abdominal wall may be referred to as peritoneal adhesions. Abdominal adhesions refers to internal scar tissue which extends from one tissue to another tissue within the abdominal and/or pelvic cavity (e.g., small intestine, large intestine, stomach, liver, gallbladder, spleen, pancreas, kidneys, adrenal glands, uterus (including Fallopian tubes and ovaries), bladder, or peritoneum. An intercostal adhesion refers to the formation of scar tissue involving the intercostal muscle (e.g., transversus thoracis muscle, sternocostal muscle, or subcostalis muscle).

"Lavage" refers to washing, flushing, or bathing of a surgical site or bodily cavity during a surgical procedure. Lavage may include intraperitoneal injections that are performed during a surgical procedure.

"During a surgical procedure" refers to any time after the surgical incision on the skin of the patient and prior to closing of the skin at the surgical site. "During a surgical procedure" includes the time after incision of the skin but before the actual procedure is performed; during the performance of the surgical procedure; after the surgical procedure is completed but before closing or suturing of the skin at the surgical site; or any combination thereof.

"Ileus" is used in accordance with its plain ordinary meaning in the medical field, and refers to a disruption of the normal propulsive ability of the gastrointestinal tract. Ileus may be caused by bowel obstruction, atony (e.g., uterine atony, gastrointestinal atony, or postoperatively gastrointestinal atony), or paralysis which may be associated with surgery (e.g., gastrointestinal surgery), electrolyte imbalance, diabetic ketoacidosis, hypothyroidism, or Ogilvie syndrome. In embodiments, ileus is a partial or complete non-mechanical obstruction of the small and/or large intestine. Ileus may be caused, for example, by manipulation of the intestines during abdominal surgery, inflammation of the peritoneum, or administration of narcotics, or chemotherapeutic agents.

"Postoperative ileus" or "postoperative paralytic ileus" refers to obstipation and intolerance of oral intake due to nonmechanical factors that disrupt the normal coordinated propulsive motor activity of the gastrointestinal tract following abdominal or nonabdominal surgery. Paralytic ileus is a common side effect of some types of surgery and does not require the intestinal paralysis need not be complete, but it must be sufficient to prohibit the passage of food through the intestine and lead to intestinal blockage. Some degree of postoperative ileus is a normal obligatory and physiologic response to abdominal surgery. Physiologic postoperative ileus is generally a benign condition that resolves without serious sequelae. However, when ileus is prolonged, it leads to patient discomfort, dissatisfaction, and prolonged hospitalization, and it must be differentiated from mechanical bowel obstruction or other postoperative complications.

"Peritoneal cavity" is used in accordance with its plain ordinary meaning in the medical field, and refers to the potential space between the parietal peritoneum and visceral peritoneum, that is, the two membranes that separate the organs in the abdominal cavity from the abdominal wall.

"Intercostal space" is used in accordance with its plain ordinary meaning in the medical field, and refers to the space between two ribs.

Pharmaceutical Compositions

In embodiments, the pharmaceutical compositions used in the methods described herein comprise tranexamic acid. In embodiments, the pharmaceutical compositions used in the methods described herein comprise tranexamic acid and one or more compounds selected from the group consisting of polyethylene glycol, glucose, electrolytes, and a combination of two or more thereof. In embodiments, the pharmaceutical compositions used in the methods described herein comprise tranexamic acid, polyethylene glycol, and at least one electrolyte. In embodiments, the pharmaceutical compositions used in the methods described herein comprise tranexamic acid, polyethylene glycol, and glucose. In embodiments, the pharmaceutical compositions used in the methods described herein comprise tranexamic acid, polyethylene glycol, glucose, and at least one electrolyte. In embodiments, the pharmaceutical compositions used in the methods described herein are in the form of an aqueous solution. In embodiments, the pharmaceutical composition is one or more compositions described in U.S. Pat. No. 9,314,442, the disclosure of which is incorporated by reference herein in its entirety. In embodiments, the pharmaceutical composition is one or more compositions described in U.S. Pat. No. 9,504,736, the disclosure of which is incorporated by reference herein in its entirety.

In embodiments, the pharmaceutical composition comprises about 1.1 wt % of tranexamic acid, about 4.6 wt % of polyethylene glycol, about 4.0 wt % of glucose, and about 0.96 wt % of at least one electrolyte. In embodiments, the pharmaceutical composition comprises about 0.9 wt % to about 1.3 wt % of tranexamic acid, about 4.4 wt % to about 4.8 wt % of polyethylene glycol, about 3.0 wt % to about 5.0 wt % of glucose, and about 0.9 wt % to about 1.0 wt % of at least one electrolyte. In embodiments, the pharmaceutical composition comprises about 0.7 wt % to about 1.5 wt % of tranexamic acid, about 4.2 wt % to about 5.0 wt % of polyethylene glycol, about 2.0 wt % to about 6.0 wt % of glucose, and about 0.8 wt % to about 1.1 wt % of at least one electrolyte. In embodiments, the pharmaceutical composition comprises about 0.4 wt % to about 1.8 wt % of tranexamic acid, about 3.9 wt % to about 5.3 wt % of polyethylene glycol, about 1.0 wt % to about 7.0 wt % of glucose, and about 0.6 wt % to about 1.3 wt % of at least one electrolyte. In embodiments, the pharmaceutical composition comprises about 0.1 wt % to about 5.0 wt % of tranexamic acid, about 0.1 wt % to about 10 wt % of polyethylene glycol, about 0.1 wt % to about 20.0 wt % of glucose, and about 0.05 wt % to about 10 wt % of at least one electrolyte.

In embodiments, the pharmaceutical composition comprises about 0.9 wt % to about 1.3 wt % of tranexamic acid, about 4.4 wt % to about 4.8 wt % of polyethylene glycol, and about 0.9 wt % to about 1.0 wt % of at least one electrolyte. In embodiments, the pharmaceutical composition comprises about 0.7 wt % to about 1.5 wt % of tranexamic acid, about 4.2 wt % to about 5.0 wt % of polyethylene glycol, and about 0.8 wt % to about 1.1 wt % of at least one electrolyte. In embodiments, the pharmaceutical composition comprises about 0.4 wt % to about 1.8 wt % of tranexamic acid, about 3.9 wt % to about 5.3 wt % of polyethylene glycol, and about 0.6 wt % to about 1.3 wt % of at least one electrolyte. In embodiments, the pharmaceutical composition comprises about 0.1 wt % to about 5.0 wt % of tranexamic acid, about 0.1 wt % to about 10 wt % of polyethylene glycol, and about 0.05 wt % to about 10 wt % of at least one electrolyte.

In embodiments, the pharmaceutical composition comprises about 0.9 wt % to about 1.3 wt % of tranexamic acid, about 3.0 wt % to about 5.0 wt % of glucose, and about 0.9 wt % to about 1.0 wt % of at least one electrolyte. In embodiments, the pharmaceutical composition comprises about 0.7 wt % to about 1.5 wt % of tranexamic acid, about 2.0 wt % to about 6.0 wt % of glucose, and about 0.8 wt % to about 1.1 wt % of at least one electrolyte. In embodiments, the pharmaceutical composition comprises about 0.4 wt % to about 1.8 wt % of tranexamic acid, about 1.0 wt % to about 7.0 wt % of glucose, and about 0.6 wt % to about 1.3 wt % of at least one electrolyte. In embodiments, the pharmaceutical composition comprises about 0.1 wt % to about 5.0 wt % of tranexamic acid, about 0.1 wt % to about 20.0 wt % of glucose, and about 0.05 wt % to about 10 wt % of at least one electrolyte.

In embodiments, the electrolyte in the pharmaceutical compositions described herein is sodium, potassium, calcium, magnesium, chloride, bicarbonate, phosphate, sulfate, or a combination of two or more thereof. In embodiments, the electrolyte is sodium, sulfate, bicarbonate, chloride, potassium, or a combination of two or more thereof. In embodiments, the electrolyte is sodium sulfate, sodium bicarbonate, sodium chloride, potassium chloride, or a combination of two or more thereof. In embodiments, the pharmaceutical composition comprises electrolytes in an amount of about 0.57 wt % of sodium sulfate, about 0.17 wt % of sodium bicarbonate, about 0.15 wt % of sodium chloride, and about 0.07 wt % of potassium chloride. In embodiments, the pharmaceutical composition comprises electrolytes in an amount of about 0.5 wt % to about 0.6 wt % of sodium sulfate, about 0.1 wt % to about 0.2 wt % of sodium bicarbonate, about 0.1 wt % to about 0.2 wt % of sodium chloride, and about 0.06 wt % to about 0.09 wt % of potassium chloride. In embodiments, the pharmaceutical composition comprises electrolytes in an amount of about 0.1 wt % to about 1.0 wt % of sodium sulfate, about 0.01 wt % to about 1.0 wt % of sodium bicarbonate, about 0.01 wt % to about 1.0 wt % of sodium chloride, and about 0.01 wt % to about 1.0 wt % of potassium chloride.

In embodiments, the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons. In embodiments, the polyethylene glycol has an average molecular weight of about 3,000 Daltons to about 4,500 Daltons. In embodiments, the polyethylene glycol has an average molecular weight of about 4,000 Daltons. In embodiments, the polyethylene glycol has an average molecular weight of about 3,350 Daltons.

In embodiments, the pharmaceutical compositions described herein have a volume of about 250 ml to about 1,000 ml, and comprise about 1.0 gram to about 10.0 grams tranexamic acid, about 5.0 grams to about 40.0 grams polyethylene glycol having a molecular weight of about 3,350, about 5 grams to about 40 grams of glucose, and about 0.01 grams to about 15.0 grams of at least one electrolyte. In embodiments, the pharmaceutical compositions described herein have a volume of about 400 ml to about 1,000 ml, and comprise about 5.0 grams to about 10.0 grams tranexamic acid, about 25.0 grams to about 40.0 grams polyethylene glycol having a molecular weight of about 3,350, about 15 grams to about 40 grams of glucose, and about 1 gram to about 15.0 grams of at least one electrolyte. In embodiments, the pharmaceutical compositions described herein have a volume of about 600 ml to about 800 ml, and comprise about 6.0 grams to about 9.0 grams tranexamic acid, about 28.0 grams to about 37.0 grams polyethylene glycol having a molecular weight of about 3,350, about 22 grams to about 34 grams of glucose, and about 4 grams to about 10.0 grams of at least one electrolyte. In embodiments, the pharmaceutical compositions described herein have a volume of about 600 ml to about 800 ml, and comprise about 6.5 grams to about 8.5 grams tranexamic acid, about 30.0 grams to about 35.0 grams polyethylene glycol having a molecular weight of about 3,350, about 25 grams to about 31 grams of glucose, about 3 grams to about 5 grams of sodium sulfate, about 0.8 grams to about 1.6 grams sodium bicarbonate, about 0.5 grams to about 1.5 grams sodium chloride, and about 0.1 grams to about 1.0 grams potassium chloride. In embodiments, the pharmaceutical compositions described herein have a volume of about 700 ml and comprise about 7.5 grams tranexamic acid, about 32.5 grams polyethylene glycol having a molecular weight of about 3,350, about 28 grams of glucose, about 4 grams of sodium sulfate, about 1.2 grams sodium bicarbonate, about 1.0 grams sodium chloride, and about 0.5 grams potassium chloride.

In embodiments, the pharmaceutical compositions described herein have a volume of about 250 ml to about 1,000 ml, and comprise about 1.0 gram to about 10.0 grams tranexamic acid, about 5.0 grams to about 40.0 grams polyethylene glycol having a molecular weight of about 3,350, and about 0.01 grams to about 15.0 grams of at least one electrolyte. In embodiments, the pharmaceutical compositions described herein have a volume of about 400 ml to about 1,000 ml, and comprise about 5.0 grams to about 10.0 grams tranexamic acid, about 25.0 grams to about 40.0 grams polyethylene glycol having a molecular weight of about 3,350, and about 1 gram to about 15.0 grams of at least one electrolyte. In embodiments, the pharmaceutical compositions described herein have a volume of about 600 ml to about 800 ml, and comprise about 6.0 grams to about 9.0 grams tranexamic acid, about 28.0 grams to about 37.0 grams polyethylene glycol having a molecular weight of about 3,350, and about 4 grams to about 10.0 grams of at least one electrolyte. In embodiments, the pharmaceutical compositions described herein have a volume of about 600 ml to about 800 ml, and comprise about 6.5 grams to about 8.5 grams tranexamic acid, about 30.0 grams to about 35.0 grams polyethylene glycol having a molecular weight of about 3,350, about 3 grams to about 5 grams of sodium sulfate, about 0.8 grams to about 1.6 grams sodium bicarbonate, about 0.5 grams to about 1.5 grams sodium chloride, and about 0.1 grams to about 1.0 grams potassium chloride.

In embodiments, the pharmaceutical compositions described herein have a volume of about 700 ml and comprise about 7.5 grams tranexamic acid, about 32.5 grams polyethylene glycol having a molecular weight of about 3,350, about 4 grams of sodium sulfate, about 1.2 grams sodium bicarbonate, about 1.0 grams sodium chloride, and about 0.5 grams potassium chloride.

In embodiments, the pharmaceutical composition is Formula A set forth in Table 1.m In embodiments, the pharmaceutical composition is Formula A set forth in Table 1 with reference to the components in weight by grams. In embodiments, the pharmaceutical composition is Formula A set forth in Table 1 with reference to the components in weight %.

The pharmaceutical compositions described herein can include a single agent (e.g., tranexamic acid) or more than one agent. The compositions for administration will commonly include an agent as described herein dissolved in a pharmaceutically acceptable carrier, preferably an aqueous carrier. A variety of aqueous carriers can be used, e.g., water, buffered saline, saline, sterile saline, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent (e.g., tranexamic acid) in these formulations can vary, and will be selected primarily based on fluid volumes, viscosities, body weight and the like in accordance with the particular mode of administration selected and the subject's needs.

The aqueous pharmaceutical compositions described herein can be presented in unit-dose or multi-dose sealed containers, such as ampules and vials. Thus, the composition can be in unit dosage form. In such form, the preparation is subdivided into unit doses containing appropriate quantities of the active component. Thus, the compositions can be administered in a variety of unit dosage forms depending upon the method of administration. In embodiments, the pharmaceutical compositions described herein are stored in two separate containers prior to administration, wherein one container comprises tranexamic acid, polyethylene glycol, and at least one electrolyte, and another container comprises glucose. Prior to oral or lavage administration, the contents of the containers are mixed together to form the pharmaceutical compositions described herein. In embodiments, the pharmaceutical compositions described herein are stored in a single container prior to administration to a patient.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art. For example, the pharmaceutical composition described herein can be administered as a single dose prior to a surgical procedure to prevent or treat adhesions or ileus, as two doses prior to a surgical procedure to prevent or treat adhesions or ileus, as three doses prior to a surgical procedure to prevent or treat adhesions or ileus, or as four doses prior to a surgical procedure to prevent or treat adhesions or ileus.

In embodiments, the pharmaceutical composition is administered as a single dose prior to a surgical procedure to prevent or treat adhesions or ileus. When administered as a single dose, the composition may be orally administered from about 8 hours to about 5 minutes prior to a surgical procedure to prevent or treat adhesions or ileus, or from about 6 hours to 5 minutes prior to a surgical procedure to prevent or treat adhesions or ileus, or from about 4 hours to about 5 minutes prior to a surgical procedure to prevent or treat adhesions or ileus, or from about 3 hours to about 5 minutes prior to a surgical procedure to prevent or treat adhesions or ileus, or from about 2 hour to about 5 minutes prior to a surgical procedure to prevent or treat adhesions or ileus, or about 1 hour to about 5 minutes prior to a surgical procedure to prevent or treat adhesions or ileus. In embodiments, the single dose is an amount of about 100 ml to about 2,000 ml; or about 200 ml to about 1,500 ml; or about 300 ml to about 1,200 ml; or about 400 ml to about 1,000 ml; or about 500 ml to about 900 ml; or about 600 ml to about 800 ml; or about 700 ml.

In embodiments, the pharmaceutical composition is administered as two doses prior to a surgical procedure to prevent or treat adhesions or ileus. When administered as two doses prior to a surgical procedure to prevent or treat adhesions or ileus, a first dose is administered about 4.1 hours to about 12 hours prior to the surgical procedure, and a second dose is administered about 4 hours to about 5 minutes prior to the surgical procedure. In other embodiments, a first dose is administered about 5 hours to about 10 hours prior to the surgical procedure, and a second dose is administered about 3 hours to about 5 minutes prior to the surgical procedure to prevent or treat adhesions or ileus. In other embodiments, a first dose is administered about 6 hours to about 8 hours prior to the surgical procedure, and a second dose is administered about 2 hours to about 5 minutes prior to the surgical procedure to prevent or treat adhesions or ileus. In other embodiments, a first dose is administered about 6 hours to about 8 hours prior to the surgical procedure, and a second dose is administered about 1 hour to about 5 minutes prior to the surgical procedure to prevent or treat adhesions or ileus. In embodiments, the first dose is about 100 ml to about 600 ml, and the second dose is about 100 ml to about 600 ml. In embodiments, the first dose is about 200 ml to about 500 ml, and the second dose is about 200 ml to about 500 ml. In embodiments, the first dose is about 250 ml to about 450 ml, and the second dose is about 250 ml to about 450 ml. In embodiments, the first dose is about 300 ml to about 400 ml, and the second dose is about 300 ml to about 400 ml. In embodiments, the first dose is about 325 ml to about 375 ml, and the second dose is about 325 ml to about 375 ml. In embodiments, the first dose is about 350 ml, and the second dose is about 350 ml.

In embodiments, the first dose is administered after completion of pre-surgical bowel preparation, and the second dose is administered prior to the surgical procedure to prevent or treat adhesions or ileus. In other embodiments, the first dose is administered about 15 minutes to about 2 hours after completion of pre-surgical bowel preparation, and the second dose is administered about 3 hours to about 5 minutes prior to the surgical procedure to prevent or treat adhesions or ileus. In other embodiments, the first dose is administered about 30 minutes to about 2 hours after completion of pre-surgical bowel preparation, and the second dose is administered about 2 hours to about 5 minutes prior to the surgical procedure to prevent or treat adhesions or ileus. In other embodiments, the first dose is administered about 30 minutes to about 1 hour after completion of pre-surgical bowel preparation, and the second dose is administered about 1 hour to about 5 minutes prior to the surgical procedure to prevent or treat adhesions or ileus. In embodiments, the first dose is about 100 ml to about 600 ml, and the second dose is about 100 ml to about 600 ml. In embodiments, the first dose is about 200 ml to about 500 ml, and the second dose is about 200 ml to about 500 ml. In embodiments, the first dose is about 250 ml to about 450 ml, and the second dose is about 250 ml to about 450 ml. In embodiments, the first dose is about 300 ml to about 400 ml, and the second dose is about 300 ml to about 400 ml. In embodiments, the first dose is about 325 ml to about 375 ml, and the second dose is about 325 ml to about 375 ml. In embodiments, the first dose is about 350 ml, and the second dose is about 350 ml. "Pre-surgical bowel preparation" refers to the cleansing or emptying of the bowels prior to surgery and is accomplished by methods known in the art. Such methods include the use of polyethylene glycol formulations, bisacodyl formulations, and the like.

Methods

The disclosure provides methods for treating and preventing adhesions or ileus in a patient in need thereof by administering to the patient a therapeutically effective amount of an aqueous pharmaceutical composition comprising tranexamic acid. In embodiments, the disclosure provides methods for treating or preventing adhesions or ileus in a patient in need thereof by administering a therapeutically effective amount of an aqueous pharmaceutical composition that comprises tranexamic acid and one or more compounds selected from the group consisting of polyethylene glycol, glucose, and an electrolyte. In embodiments, the disclosure provides methods for treating or preventing adhesions or ileus in a patient in need thereof by administering a therapeutically effective amount of an aqueous pharmaceutical composition comprises tranexamic acid, polyethylene glycol, and at least one electrolyte. In embodiments, the disclosure provides methods for treating or preventing adhesions or ileus in a patient in need thereof by administering a therapeutically effective amount of an aqueous pharmaceutical composition comprises tranexamic acid, glucose, and at least one electrolyte. In embodiments, the disclosure provides methods for treating and preventing adhesions or ileus in a patient in need thereof by administering a therapeutically effective amount of an aqueous pharmaceutical composition comprises tranexamic acid, polyethylene glycol, and glucose. In embodiments, the disclosure provides methods for treating and preventing adhesions or ileus in a patient in need thereof by administering a therapeutically effective amount of an aqueous pharmaceutical composition comprises tranexamic acid, polyethylene glycol, glucose, and at least one electrolyte.

The disclosure provides methods for treating and preventing adhesions or ileus in a patient in need thereof by orally administering to the patient a therapeutically effective amount of an aqueous pharmaceutical composition containing tranexamic acid, where the aqueous pharmaceutical composition is orally administered to the patient prior to a surgical procedure. In embodiments, the disclosure provides methods for treating adhesions or ileus in a patient in need thereof by orally administering a therapeutically effective amount of an aqueous pharmaceutical composition that comprises tranexamic acid and one or more compounds selected from the group consisting of polyethylene glycol, glucose, and an electrolyte; and where the aqueous pharmaceutical composition is orally administered to the patient prior to a surgical procedure. In embodiments, the disclosure provides methods for treating adhesions or ileus in a patient in need thereof by orally administering a therapeutically effective amount of an aqueous pharmaceutical composition that comprises tranexamic acid, polyethylene glycol, and at least one electrolyte; and where the aqueous pharmaceutical composition is orally administered to the patient prior to a surgical procedure. In embodiments, the disclosure provides methods for treating and preventing adhesions or ileus in a patient in need thereof by orally administering a therapeutically effective amount of an aqueous pharmaceutical composition that comprises tranexamic acid, glucose, and at least one electrolyte; and where the aqueous pharmaceutical composition is orally administered to the patient prior to a surgical procedure. In embodiments, the disclosure provides methods for treating and preventing adhesions or ileus in a patient in need thereof by orally administering a therapeutically effective amount of an aqueous pharmaceutical composition that comprises tranexamic acid, polyethylene glycol, and glucose; and where the aqueous pharmaceutical composition is orally administered to the patient prior to a surgical procedure.

In embodiments, the disclosure provides methods for treating and preventing adhesions in a patient in need thereof by orally administering a therapeutically effective amount of an aqueous pharmaceutical composition that comprises tranexamic acid, polyethylene glycol, glucose, and at least one electrolyte; and where the aqueous pharmaceutical composition is orally administered to the patient prior to a surgical procedure. In embodiments, the methods may optionally further include orally administering the aqueous pharmaceutical composition to the patient after the surgical procedure. "After" includes any time from about 1 hour after the surgical procedure to about 1 week after the surgical procedure.

In embodiments, the disclosure provides methods for treating and preventing ileus in a patient in need thereof by orally administering a therapeutically effective amount of an aqueous pharmaceutical composition comprises tranexamic acid, polyethylene glycol, and at least one electrolyte, where the aqueous pharmaceutical composition is orally administered to the patient prior to a surgical procedure. In embodiments, the disclosure provides methods for treating and preventing ileus in a patient in need thereof by orally administering a therapeutically effective amount of an aqueous pharmaceutical composition comprises tranexamic acid, glucose, and at least one electrolyte, where the aqueous pharmaceutical composition is orally administered to the patient prior to a surgical procedure. In embodiments, the disclosure provides methods for treating and preventing ileus in a patient in need thereof by orally administering a therapeutically effective amount of an aqueous pharmaceutical composition comprises tranexamic acid, polyethylene glycol, and glucose, where the aqueous pharmaceutical composition is orally administered to the patient prior to a surgical procedure. In embodiments, the disclosure provides methods for treating and preventing ileus in a patient in need thereof by orally administering a therapeutically effective amount of an aqueous pharmaceutical composition comprises tranexamic acid, polyethylene glycol, glucose, and at least one electrolyte, where the aqueous pharmaceutical composition is orally administered to the patient prior to a surgical procedure. In embodiments, the methods may optionally further include orally administering the aqueous pharmaceutical composition to the patient after the surgical procedure. "After" includes any time from about 1 hour after the surgical procedure to about 1 week after the surgical procedure.

In embodiments, the methods for treating and preventing adhesions include, but are not limited to methods of reducing the incidence of adhesions; methods of reducing the number of adhesions; methods of reducing the severity of adhesions; methods of reducing the thickness of adhesions; methods of preventing the formation of adhesions; and combination of two or more thereof. In embodiments, the method for treating and preventing adhesions is a method of reducing the incidence of adhesions. In embodiments, the method for treating and preventing adhesions is a method of reducing the number of adhesions. In embodiments, the method for treating and preventing adhesions is a method of reducing the severity of adhesions. In embodiments, the method for treating and preventing adhesions is a method of reducing the thickness of adhesions. In embodiments, the method for treating and preventing adhesions is a method of reducing the incidence and reducing the number of adhesions. In embodiments, the method for treating and preventing adhesions is a method of reducing the incidence and reducing the severity of adhesions. In embodiments, the method for treating and preventing adhesions is a method of reducing the incidence and reducing the thickness of adhesions. In embodiments, the method for treating and preventing adhesions is a method of reducing the severity and reducing the thickness of adhesions. In embodiments, the method for treating and preventing adhesions is a method of reducing the incidence, reducing the number, and reducing the severity of adhesions. In embodiments, the method for treating and preventing adhesions is a method of reducing the incidence, reducing the number, and reducing the thickness of adhesions. In embodiments, the disclosure provides methods for preventing the formation of adhesions. In embodiments, the methods for treating ileus include, but are not limited to methods of reducing the severity of ileus, and methods of decreasing the duration of ileus. In embodiments, the disclosure provides methods for preventing ileus.

In embodiments, the method reduces about 5%, about 10%, about 15%, about 20%, about 25%, about 40%, about 50%, about 60%, about 75%, about 80%, about 90%, or about 100% of the original number of adhesions. In embodiments, the method reduces about 5%, about 10%, about 15%, about 20%, about 25%, about 40%, about 50%, about 60%, about 75%, about 80%, about 90%, or about 100% of the original thickness of adhesions. Efficacy can also be expressed as "fold" increase or decrease. For example, the method can have at least a 1.2-fold, 1.5-fold, 2-fold, 5-fold, or more effect over a control.

In embodiments, the method includes administering the composition to the patient by lavage. In embodiments, the method includes administering the composition to the intercostal space of the patient by lavage. In embodiments, the method includes administering the composition to the peritoneal cavity of the patient by lavage. In embodiments, the method includes administering the composition to the stomach, to the intestines, or to the stomach and intestines. In embodiments, the method includes administering the composition to the stomach. In embodiments, the method includes administering the composition to the intestines. In embodiments, the method includes administering the composition to the stomach and intestines. When the compositions are administered to the patient by lavage, the compositions are administered during a surgical procedure.

In embodiments of treating or preventing adhesions or ileus, the methods include orally administering the aqueous pharmaceutical composition to the patient. In embodiments of treating or preventing adhesions or ileus, the methods include orally administering the aqueous pharmaceutical composition to the patient before a surgical procedure. In embodiments of treating or preventing adhesions or ileus, the methods include orally administering the aqueous pharmaceutical composition to the patient after a surgical procedure. In embodiments of treating or preventing adhesions or ileus, the methods include orally administering the aqueous pharmaceutical composition to the patient before and after a surgical procedure. It has been unexpectedly discovered that the pharmaceutical compositions described herein can be orally administered to the patient and effectively treat and prevent adhesions or ileus, as described herein. In embodiments, the methods are for treating adhesions. In embodiments, the methods are for preventing adhesions. In embodiments, the methods are for treating and preventing adhesions. In embodiments, the methods are for treating ileus. In embodiments, the methods are for preventing ileus. In embodiments, the methods are for treating and preventing ileus.

In embodiments of treating and preventing adhesions or ileus, the methods include orally administering the aqueous pharmaceutical composition described herein to the patient prior to a surgical procedure, and subsequently orally administering a therapeutically effective amount of a second aqueous pharmaceutical composition containing tranexamic acid to the patient after the surgical procedure. In embodiments, the second aqueous pharmaceutical composition contains tranexamic acid, but does not contain polyethylene glycol or glucose. In embodiments, the second aqueous pharmaceutical composition contains tranexamic acid and a saline solution. In embodiments, the pharmaceutical composition administered before and after surgery is the same composition.

In embodiments of treating and preventing adhesions or ileus, the method includes orally administering the aqueous pharmaceutical composition described herein to the patient prior to a surgical procedure, and subsequently orally administering a therapeutically effective amount of the same aqueous pharmaceutical composition containing tranexamic acid, polyethylene glycol, glucose, and at least one electrolyte, to the patient after the surgical procedure. In embodiments of treating and preventing adhesions or ileus, the method includes orally administering the aqueous pharmaceutical composition described herein to the patient prior to a surgical procedure, and subsequently orally administering a therapeutically effective amount of a different aqueous pharmaceutical composition containing tranexamic acid, and one or more compounds selected from the group consisting of polyethylene glycol, glucose, and at least one electrolyte, to the patient after the surgical procedure.

In embodiments, the methods include orally administering the aqueous pharmaceutical composition described herein to the patient prior to a surgical procedure, and subsequently administering a therapeutically effective amount of a second aqueous pharmaceutical composition containing tranexamic acid to the patient by lavage during a surgical procedure. In embodiments, the second aqueous pharmaceutical composition contains tranexamic acid, but does not contain polyethylene glycol or glucose. In embodiments, the second aqueous pharmaceutical composition contains tranexamic acid and a saline solution. In embodiments, the orally administered pharmaceutical composition and the second aqueous pharmaceutical composition administered by lavage comprise the same compounds in the same amounts.

In embodiments, the method includes orally administering the aqueous pharmaceutical composition described herein to the patient prior to a surgical procedure, and subsequently administering a therapeutically effective amount of the same aqueous pharmaceutical composition containing tranexamic acid, polyethylene glycol, glucose, and at least one electrolyte, to the patient by lavage prior to or during a surgical procedure. In embodiments, the method includes orally administering the aqueous pharmaceutical composition described herein to the patient prior to a surgical procedure, and subsequently administering a therapeutically effective amount of a different aqueous pharmaceutical composition containing tranexamic acid, and one or more compounds selected from the group consisting of polyethylene glycol, glucose, and at least one electrolyte, to the patient by lavage during a surgical procedure.

In embodiments, the second aqueous pharmaceutical composition is administered to the peritoneal cavity of the patient. In embodiments, the second aqueous pharmaceutical composition is administered to the patient by lavage to the stomach, by lavage to the intestines, or by lavage to the stomach and intestines. In embodiments, the second aqueous pharmaceutical composition is administered to the patient by lavage to the stomach. In embodiments, the second aqueous pharmaceutical composition is administered to the patient by lavage to the intestines. In embodiments, the second aqueous pharmaceutical composition is administered to the patient by lavage to the stomach and intestines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

The following embodiments are for purposes of illustration only, and the disclosure is not intended to be limited by these particularly exemplified embodiments.

Embodiment P1

A method for treating or preventing adhesions in a patient in need thereof comprising administering to the patient a therapeutically effective amount of an aqueous pharmaceutical composition comprising tranexamic acid, polyethylene glycol, glucose, and at least one electrolyte.

Embodiment P2

The method of Embodiment P1, wherein the aqueous pharmaceutical composition is administered to the patient prior to a surgical procedure.

Embodiment P3

A method for treating or preventing adhesions in a patient in need thereof comprising orally administering to the patient a therapeutically effective amount of an aqueous pharmaceutical composition prior to a surgical procedure to treat or prevent adhesions; wherein the aqueous pharmaceutical composition comprises tranexamic acid, polyethylene glycol, glucose, and at least one electrolyte.

Embodiment P4

The method of Embodiment P1 or P3, wherein the adhesions are surgical adhesions.

Embodiment P5

The method of Embodiment P1 or P3, wherein the adhesions are abdominal adhesions.

Embodiment P6

The method of Embodiment P1 or P3, wherein the adhesions are intestinal adhesions.

Embodiment P7

The method of Embodiment P1 or P3, wherein the adhesions are peritoneal adhesions.

Embodiment P8

The method of Embodiment P1 or P3, wherein the adhesions are intercostal adhesions.

Embodiment P9

The method of Embodiment P1 or P3, wherein the adhesions are abdominal adhesions, intestinal adhesions, peritoneal adhesions, or a combination of two or more thereof.

Embodiment P10

The method of any one of Embodiments P1-P9, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment P11

The method of any one of Embodiments P1-P10, wherein treating or preventing adhesions comprises reducing the number of adhesions, reducing the severity of adhesions, or a combination thereof.

Embodiment P12

The method of any one of Embodiments P1-P9, wherein treating or preventing adhesions comprises reducing a complication caused by adhesions or reducing a co-morbidity caused by adhesions.

Embodiment P13

The method of Embodiment P12, wherein the complication caused by adhesions is an intestinal obstruction, infertility, pain, or a combination of two or more thereof.

Embodiment P14

The method of any one of Embodiments P1, P2 and P4-P13, comprising orally administering the composition to the patient.

Embodiment P15

The method of Embodiment P2, P3 or P14, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P16

The method of any one of Embodiments P1, P2 and P4-P13, comprising administering the composition to the patient by lavage.

Embodiment P17

The method of Embodiment P16, comprising administering the composition to the peritoneal cavity of the patient by lavage.

Embodiment P18

The method of Embodiment P16, comprising administering the composition to an intercostal space in the patient.

Embodiment P19

The method of Embodiment P16, comprising administering the composition to the stomach, to the intestines, or to the stomach and intestines.

Embodiment P20

The method of Embodiment P16, comprising administering the composition to the patient by lavage during a surgical procedure.

Embodiment P21

The method of any one of Embodiments P1-P20, wherein the pharmaceutical composition comprises about 1.1 wt % of tranexamic acid, about 4.6 wt % of polyethylene glycol, about 4.0 wt % of glucose, and about 0.96 wt % of at least one electrolyte.

Embodiment P22

The method of any one of Embodiments P1-P20, wherein the pharmaceutical composition comprises about 1.1 wt % of tranexamic acid, about 4.6 wt % of polyethylene glycol having an average molecular weight of about 3,350, about 4.0 wt % of glucose, about 0.57 wt % of sodium sulfate, about 0.17 wt % of sodium bicarbonate, about 0.15 wt % of sodium chloride, and about 0.07 wt % of potassium chloride.

Embodiment P23

The method of any one of Embodiments P1-P20, wherein the pharmaceutical composition comprises about 0.9 wt % to about 1.3 wt % of tranexamic acid, about 4.4 wt % to about 4.8 wt % of polyethylene glycol, about 3.0 wt % to about 5.0 wt % of glucose, and about 0.9 wt % to about 1.0 wt % of at least one electrolyte.

Embodiment P24

The method of any one of Embodiments P1-P20, wherein the pharmaceutical composition comprises about 0.7 wt % to about 1.5 wt % of tranexamic acid, about 4.2 wt % to about 5.0 wt % of polyethylene glycol, about 2.0 wt % to about 6.0 wt % of glucose, and about 0.8 wt % to about 1.1 wt % of at least one electrolyte.

Embodiment P25

The method of any one of Embodiments P1-P20, wherein the pharmaceutical composition comprises about 0.4 wt % to about 1.8 wt % of tranexamic acid, about 3.9 wt % to about 5.3 wt % of polyethylene glycol, about 1.0 wt % to about 7.0 wt % of glucose, and about 0.6 wt % to about 1.3 wt % of at least one electrolyte.

Embodiment P26

The method of any one of Embodiments P1-P21 and P23-P25, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P27

The method of any one of Embodiments P1-P21 and P23-P25, wherein the polyethylene glycol has an average molecular weight of about 3,350 Daltons.

Embodiment P28

The method of any one of Embodiments P1-P21 and P23-P27, wherein the electrolyte is sodium, potassium, calcium, magnesium, chloride, bicarbonate, phosphate, sulfate, or a combination of two or more thereof.

Embodiment 29

The method of any one of Embodiments P1-P21 and P23-P27 wherein the electrolyte is sodium, sulfate, bicarbonate, chloride, potassium, or a combination of two or more thereof.

Embodiment P30

The method of any one of Embodiments P1-P21 and P23-P27, wherein the electrolyte is sodium sulfate, sodium bicarbonate, sodium chloride, potassium chloride, or a combination of two or more thereof.

Embodiment P31

The method of any one of Embodiments P1-P30, wherein the volume of the aqueous pharmaceutical composition is about 700 mL.

Embodiment P32

The method of any one of Embodiments P1-P30, wherein the volume of the aqueous pharmaceutical composition is about 500 mL to about 900 mL.

Embodiment P33

The method of any one of Embodiments P1-P30, wherein the volume of the aqueous pharmaceutical composition is about 300 mL to about 1,000 mL.

Embodiment P34

The method of any one of Embodiments P1-P30, wherein the volume of the aqueous pharmaceutical composition is about 100 mL to about 2,000 mL.

Embodiment P35

The method of any one of Embodiments P1-P20, wherein the pharmaceutical composition has a volume of about 600 ml to about 800 ml, and comprises about 6.0 grams to about 9.0 grams tranexamic acid, about 28.0 grams to about 37.0 grams polyethylene glycol having a molecular weight of about 3,350, about 22 grams to about 34 grams of glucose, and about 4 grams to about 10.0 grams of at least one electrolyte.

Embodiment P36

The method of any one of Embodiments P1-P20, wherein the pharmaceutical composition has a volume of about 700 ml, and comprises about 7.5 grams tranexamic acid, about 32.5 grams polyethylene glycol having a molecular weight of about 3,350, about 28 grams of glucose, about 4 grams of sodium sulfate, about 1.2 grams sodium bicarbonate, about 1.0 grams sodium chloride, and about 0.5 grams potassium chloride.

Embodiment P37

The method of any one of Embodiments P1-P36, further comprising orally administering to the patient or administering to the patient by lavage a therapeutically effective amount of a second aqueous pharmaceutical composition comprising tranexamic acid.

Embodiment P38

The method of Embodiment P37, wherein the second aqueous pharmaceutical composition comprises tranexamic acid and one or more compounds selected from the group consisting of polyethylene glycol, glucose, and an electrolyte.

Embodiment P39

The method of Embodiment P37, wherein the second aqueous pharmaceutical composition comprises tranexamic acid, polyethylene glycol, and at least one electrolyte.

Embodiment P40

The method of Embodiment P37, wherein the second aqueous pharmaceutical composition comprises tranexamic acid, polyethylene glycol, glucose, and at least one electrolyte.

Embodiment P41

The method of Embodiment P37, wherein the second aqueous pharmaceutical composition comprises tranexamic acid, but does not further comprise (i) polyethylene glycol, (ii) glucose, or (iii) polyethylene glycol and glucose.

Embodiment P42

The method of Embodiment P37, wherein the second aqueous pharmaceutical composition is administered to the peritoneal cavity of the patient.

Embodiment P43

The method of Embodiment P37, wherein the second aqueous pharmaceutical composition is administered to the patient by lavage to the stomach, by lavage to the intestines, or by lavage to the stomach and intestines.

Embodiment P44

The method of Embodiment P37, wherein the second aqueous pharmaceutical composition is administered to an intercostal space of the patient.

Embodiment P45

The method of Embodiments P37, wherein the second aqueous pharmaceutical composition is administered to the patient by lavage during a surgical procedure.

Embodiment P46

The method of Embodiment P37, wherein the second aqueous pharmaceutical composition is orally administered to the patient.

Embodiment P47

A method for treating or preventing adhesions in a patient in need thereof comprising administering to the patient a therapeutically effective amount of an aqueous pharmaceutical composition comprising tranexamic acid, polyethylene glycol, and at least one electrolyte.

Embodiment P48

The method of Embodiment P47, wherein the aqueous pharmaceutical composition is administered to the patient prior to a surgical procedure.

Embodiment P49

A method for treating or preventing adhesions in a patient in need thereof comprising orally administering to the patient a therapeutically effective amount of an aqueous pharmaceutical composition prior to a surgical procedure to treat or prevent adhesions; wherein the aqueous pharmaceutical composition comprises tranexamic acid, polyethylene glycol, and at least one electrolyte.

Embodiment P50

The method of Embodiment P47 or P49, wherein the adhesions are surgical adhesions.

Embodiment P51

The method of Embodiment P47 or P49, wherein the adhesions are abdominal adhesions.

Embodiment P52

The method of Embodiment P47 or P49, wherein the adhesions are intestinal adhesions.

Embodiment P53

The method of Embodiment P47 or P49, wherein the adhesions are peritoneal adhesions.

Embodiment P54

The method of Embodiment P47 or P49, wherein the adhesions are intercostal adhesions.

Embodiment P55

The method of Embodiment P47 or P49, wherein the adhesions are abdominal adhesions, intestinal adhesions, peritoneal adhesions, or a combination of two or more thereof.

Embodiment P56

The method of any one of Embodiments P47 or P49, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment P57

The method of any one of Embodiments P47 or P49, wherein treating or preventing adhesions comprises reducing the number of adhesions, reducing the severity of adhesions, or a combination thereof.

Embodiment P58

The method of any one of Embodiments P47 or P49, wherein treating or preventing adhesions comprises reducing a complication caused by adhesions or reducing a co-morbidity caused by adhesions.

Embodiment P59

The method of Embodiment P58, wherein the complication caused by adhesions is an intestinal obstruction, infertility, pain, or a combination of two or more thereof.

Embodiment P60

The method of any one of Embodiments P47, P48, and P50-P59, comprising orally administering the composition to the patient.

Embodiment P61

The method of Embodiment P48, P49, or P60, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P62

The method of any one of Embodiments P47, P48, and P49-P59, comprising administering the composition to the patient by lavage.

Embodiment P63

The method of Embodiment P62, comprising administering the composition to the peritoneal cavity of the patient by lavage.

Embodiment P64

The method of Embodiment P62, comprising administering the composition to an intercostal space in the patient.

Embodiment P65

The method of Embodiment P62, comprising administering the composition to the stomach, to the intestines, or to the stomach and intestines.

Embodiment P66

The method of Embodiment P62, comprising administering the composition to the patient by lavage during a surgical procedure.

Embodiment P67

The method of any one of Embodiments P47-P66, wherein the pharmaceutical composition comprises about 0.9 wt % to about 1.3 wt % of tranexamic acid, about 4.4 wt % to about 4.8 wt % of polyethylene glycol, and about 0.9 wt % to about 1.0 wt % of at least one electrolyte.

Embodiment P68

The method of any one of Embodiments P47-P66, wherein the pharmaceutical composition comprises about 0.7 wt % to about 1.5 wt % of tranexamic acid, about 4.2 wt % to about 5.0 wt % of polyethylene glycol, and about 0.8 wt % to about 1.1 wt % of at least one electrolyte.

Embodiment P69

The method of any one of Embodiments P47-P66, wherein the pharmaceutical composition comprises about 0.4 wt % to about 1.8 wt % of tranexamic acid, about 3.9 wt % to about 5.3 wt % of polyethylene glycol, and about 0.6 wt % to about 1.3 wt % of at least one electrolyte.

Embodiment P70

The method of any one of Embodiments P47-P66, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P71

The method of any one of Embodiments P47-P66, wherein the polyethylene glycol has an average molecular weight of about 3,350 Daltons.

Embodiment P72

The method of any one of Embodiments P47-P71, wherein the electrolyte is sodium, potassium, calcium, magnesium, chloride, bicarbonate, phosphate, sulfate, or a combination of two or more thereof.

Embodiment P73

The method of any one of Embodiments P47-P71, wherein the electrolyte is sodium, sulfate, bicarbonate, chloride, potassium, or a combination of two or more thereof.

Embodiment P74

The method of any one of Embodiments P47-P71, wherein the electrolyte is sodium sulfate, sodium bicarbonate, sodium chloride, potassium chloride, or a combination of two or more thereof.

Embodiment P75

The method of any one of Embodiments P47-P74, wherein the volume of the aqueous pharmaceutical composition is about 700 mL.

Embodiment P76

The method of any one of Embodiments P47-P74, wherein the volume of the aqueous pharmaceutical composition is about 500 mL to about 900 mL; or about 300 mL to about 1,000 mL; or about 100 mL to about 2,000 mL.

Embodiment P77

The method of any one of Embodiments P47-P76, further comprising orally administering to the patient after the surgical procedure or administering to the patient by lavage a therapeutically effective amount of a second aqueous pharmaceutical composition comprising tranexamic acid.

Embodiment P78

The method of Embodiment P77, wherein the second aqueous pharmaceutical composition comprises tranexamic acid and one or more compounds selected from the group consisting of polyethylene glycol, glucose, and an electrolyte.

Embodiment P79

The method of Embodiment P77, wherein the second aqueous pharmaceutical composition comprises tranexamic acid, polyethylene glycol, and at least one electrolyte.

Embodiment P80

The method of Embodiment P77, wherein the second aqueous pharmaceutical composition comprises tranexamic acid, polyethylene glycol, glucose, and at least one electrolyte.

Embodiment P81

The method of Embodiment P77, wherein the second aqueous pharmaceutical composition comprises tranexamic acid, but does not further comprise (i) polyethylene glycol, (ii) glucose, or (iii) polyethylene glycol and glucose.

Embodiment P82

The method of any one of Embodiments P77, wherein the second aqueous pharmaceutical composition is administered to the peritoneal cavity of the patient.

Embodiment P83

The method of any one of Embodiments P77, wherein the second aqueous pharmaceutical composition is administered to the patient by lavage to the stomach, by lavage to the intestines, or by lavage to the stomach and intestines.

Embodiment P84

The method of any one of Embodiments P77, wherein the second aqueous pharmaceutical composition is administered to an intercostal space of the patient.

Embodiment P85

The method of any one of Embodiments P77, wherein the second aqueous pharmaceutical composition is administered to the patient by lavage during a surgical procedure.

Embodiment P86

The method of Embodiment P77, wherein the second aqueous pharmaceutical composition is orally administered to the patient after the surgical procedure.

Embodiment P87

A method for treating or preventing adhesions in a patient in need thereof comprising administering to the patient a therapeutically effective amount of an aqueous pharmaceutical composition comprising tranexamic acid, and optionally one or more compounds selected from the group consisting of polyethylene glycol, glucose, and at least one electrolyte.

Embodiment P88

The method of Embodiment P87, wherein the aqueous pharmaceutical composition is administered to the patient prior to a surgical procedure.

Embodiment P89

A method for treating or preventing adhesions in a patient in need thereof comprising orally administering to the patient a therapeutically effective amount of an aqueous pharmaceutical composition prior to a surgical procedure to treat or prevent adhesions; wherein the aqueous pharmaceutical composition comprises tranexamic acid, and optionally one or more compounds selected from the group consisting of polyethylene glycol, glucose, and at least one electrolyte.

Embodiment 90

The method of Embodiment P87 or P89, wherein the adhesions are surgical adhesions, abdominal adhesions, intestinal adhesions, peritoneal adhesions, intercostal adhesions, or a combination of two or more thereof.

Embodiment P91

The method of Embodiment P87 or P89, wherein the adhesions are abdominal adhesions, intestinal adhesions, peritoneal adhesions, or a combination of two or more thereof.

Embodiment P92

The method of Embodiment P87 or P89, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment P93

The method of Embodiment P87 or P89, wherein treating or preventing adhesions comprises reducing the number of adhesions, reducing the severity of adhesions, or a combination thereof.

Embodiment P94

The method of Embodiment P87 or P89, wherein treating or preventing adhesions comprises reducing a complication caused by adhesions or reducing a co-morbidity caused by adhesions.

Embodiment P95

The method of Embodiment P94, wherein the complication caused by adhesions is an intestinal obstruction, infertility, pain, or a combination of two or more thereof.

Embodiment P96

The method of any one of Embodiments P87, P88, and P90-P95, comprising orally administering the composition to the patient.

Embodiment P97

The method of Embodiment P88, P89, or P96, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P98

The method of any one of Embodiments P87, P88, or P90-P95, comprising administering the composition to the patient by lavage.

Embodiment P99

The method of Embodiment P98, comprising administering the composition to the peritoneal cavity of the patient by lavage.

Embodiment P100

The method of Embodiment P98, comprising administering the composition to the stomach, to the intestines, or to the stomach and intestines.

Embodiment P101

The method of Embodiment P98, comprising administering the composition to the patient by lavage during a surgical procedure.

Embodiment P102

The method of any one of Embodiments P87-P101, wherein the pharmaceutical composition comprises tranexamic acid and polyethylene glycol.

Embodiment P103

The method of any one of Embodiments P87-P101, wherein the pharmaceutical composition comprises tranexamic acid and glucose.

Embodiment P104

The method of any one of Embodiments P87-P101, wherein the pharmaceutical composition comprises tranexamic acid and at least one electrolyte.

Embodiment P105

The method of any one of Embodiments P87-P101, wherein the pharmaceutical composition comprises tranexamic acid, glucose, and at least one electrolyte.

Embodiment P106

The method of any one of Embodiments P87-P101, wherein the pharmaceutical composition comprises tranexamic acid, polyethylene glycol, and at least one electrolyte.

Embodiment P107

The method of any one of Embodiments P87-P102 and P106, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P108

The method of any one of Embodiment P87-P102 and P106, wherein the polyethylene glycol has an average molecular weight of about 3,350 Daltons.

Embodiment P109

The method of any one of Embodiments P87-P101 and P104-P106, wherein the electrolyte is sodium, potassium, calcium, magnesium, chloride, bicarbonate, phosphate, sulfate, or a combination of two or more thereof.

Embodiment P110

The method of any one of Embodiments P87-P101 and P104-P106, wherein the electrolyte is sodium, sulfate, bicarbonate, chloride, potassium, or a combination of two or more thereof.

Embodiment P111

The method of any one of Embodiments P87-P101 and P104-P106, wherein the electrolyte is sodium sulfate, sodium bicarbonate, sodium chloride, potassium chloride, or a combination of two or more thereof.

Embodiment P112

The method of any one of Embodiments P87-P111, wherein the volume of the aqueous pharmaceutical composition is about 700 mL.

Embodiment P113

The method of any one of Embodiments P87-P111, wherein the volume of the aqueous pharmaceutical composition is about 100 mL to about 2,000 mL; or about 300 mL to about 1,000 mL; or about 500 mL to about 900 mL.

Embodiment P114

The method of any one of Embodiments P87-P113, further comprising orally administering to the patient after a surgical procedure or administering to the patient by lavage a therapeutically effective amount of a second aqueous pharmaceutical composition comprising tranexamic acid.

Embodiment P115

The method of Embodiment P114, wherein the second aqueous pharmaceutical composition comprises tranexamic acid and one or more compounds selected from the group consisting of polyethylene glycol, glucose, and an electrolyte.

Embodiment P116

The method of Embodiment P114, wherein the second aqueous pharmaceutical composition comprises tranexamic acid, polyethylene glycol, and at least one electrolyte.

Embodiment P117

The method of Embodiment P114, wherein the second aqueous pharmaceutical composition comprises tranexamic acid, polyethylene glycol, glucose, and at least one electrolyte.

Embodiment P118

The method of Embodiment P114, wherein the second aqueous pharmaceutical composition comprises tranexamic acid, but does not further comprise (i) polyethylene glycol, (ii) glucose, or (iii) polyethylene glycol and glucose.

Embodiment P119

The method of Embodiment P114, wherein the second aqueous pharmaceutical composition is administered to the peritoneal cavity of the patient.

Embodiment P120

The method of Embodiment P114, wherein the second aqueous pharmaceutical composition is administered to the patient by lavage to the stomach, by lavage to the intestines, or by lavage to the stomach and intestines.

Embodiment P121

The method of Embodiment P114, wherein the second aqueous pharmaceutical composition is administered to the patient by lavage during a surgical procedure.

Embodiment P122

The method of Embodiment P114, comprising orally administering the second aqueous pharmaceutical composition to the patient after the surgical procedure.

Embodiment P123

A method for treating or preventing ileus in a patient in need thereof comprising administering to the patient a therapeutically effective amount of an aqueous pharmaceutical composition comprising tranexamic acid, polyethylene glycol, glucose, and at least one electrolyte.

Embodiment P124

The method of Embodiment 123, wherein the aqueous pharmaceutical composition is administered to the patient prior to a surgical procedure.

Embodiment P125

A method for treating or preventing ileus in a patient in need thereof comprising orally administering to the patient a therapeutically effective amount of an aqueous pharmaceutical composition prior to a surgical procedure to treat or prevent ileus; wherein the aqueous pharmaceutical composition comprises tranexamic acid, polyethylene glycol, glucose, and at least one electrolyte.

Embodiment P126

The method of Embodiment 123 or 125, wherein the ileus is post-operative ileus.

Embodiment P127

The method of Embodiment 123 or 125, wherein the method for treating or preventing ileus comprises reducing the severity of ileus, decreasing the duration of ileus, or a combination thereof.

Embodiment P128

The method of Embodiment 123 or 125, wherein the method for treating or preventing ileus comprises reducing a complication caused by ileus or to reduce a co-morbidity caused by ileus in a patient in need thereof.

Embodiment P129

The method of Embodiment 123 or 125, wherein the method for treating or preventing ileus comprises on or more of the following: (i) increasing water consumption in the patient; (ii) increasing food consumption in the patient; (iii) increasing fecal production by the patient; (iv) increasing body weight in the patient; and (v) increasing the activity index of the patient.

Embodiment P130

The method of Embodiment 123 or 125 for preventing ileus.

Embodiment P131

The method of any one of Embodiments P123, P124, and P126-P130, comprising orally administering the composition to the patient.

Embodiment P132

The method of Embodiment P123, P125 or P131, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P133

The method of any one of Embodiments P123, P124, and P126-P130, comprising administering the composition to the patient by lavage.

Embodiment P134

The method of Embodiment P133, comprising administering the composition to the peritoneal cavity of the patient by lavage.

Embodiment P135

The method of Embodiment P133, comprising administering the composition to the stomach, to the intestines, or to the stomach and intestines.

Embodiment P136

The method of Embodiment P133, comprising administering the composition to the patient by lavage during a surgical procedure.

Embodiment P137

The method of any one of Embodiments P123-P136, wherein the pharmaceutical composition comprises about 1.1 wt % of tranexamic acid, about 4.6 wt % of polyethylene glycol, about 4.0 wt % of glucose, and about 0.96 wt % of at least one electrolyte.

Embodiment P138

The method of any one of Embodiments P123-P136, wherein the pharmaceutical composition comprises about 1.1 wt % of tranexamic acid, about 4.6 wt % of polyethylene glycol having an average molecular weight of about 3,350, about 4.0 wt % of glucose, about 0.57 wt % of sodium sulfate, about 0.17 wt % of sodium bicarbonate, about 0.15 wt % of sodium chloride, and about 0.07 wt % of potassium chloride.

Embodiment P139

The method of any one of Embodiments P123-P136, wherein the pharmaceutical composition comprises about 0.9 wt % to about 1.3 wt % of tranexamic acid, about 4.4 wt % to about 4.8 wt % of polyethylene glycol, about 3.0 wt % to about 5.0 wt % of glucose, and about 0.9 wt % to about 1.0 wt % of at least one electrolyte.

Embodiment P140

The method of any one of Embodiments P123-P136, wherein the pharmaceutical composition comprises about 0.7 wt % to about 1.5 wt % of tranexamic acid, about 4.2 wt % to about 5.0 wt % of polyethylene glycol, about 2.0 wt % to about 6.0 wt % of glucose, and about 0.8 wt % to about 1.1 wt % of at least one electrolyte.

Embodiment P141

The method of any one of Embodiments P123-P136, wherein the pharmaceutical composition comprises about 0.4 wt % to about 1.8 wt % of tranexamic acid, about 3.9 wt % to about 5.3 wt % of polyethylene glycol, about 1.0 wt % to about 7.0 wt % of glucose, and about 0.6 wt % to about 1.3 wt % of at least one electrolyte.

Embodiment P142

The method of any one of Embodiments P123-P137 and P139-P141, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P143

The method of any one of Embodiments P123-P137 and P139-P141, wherein the polyethylene glycol has an average molecular weight of about 3,350 Daltons.

Embodiment P144

The method of any one of Embodiments P123-P137 and P139-P141, wherein the electrolyte is sodium, potassium, calcium, magnesium, chloride, bicarbonate, phosphate, sulfate, or a combination of two or more thereof.

Embodiment P145

The method of any one of Embodiments P123-P137 and P139-P141, wherein the electrolyte is sodium, sulfate, bicarbonate, chloride, potassium, or a combination of two or more thereof.

Embodiment P146

The method of any one of Embodiments P123-P137 and P139-P141, wherein the electrolyte is sodium sulfate, sodium bicarbonate, sodium chloride, potassium chloride, or a combination of two or more thereof.

Embodiment P147

The method of any one of Embodiments P123-P146, wherein the volume of the aqueous pharmaceutical composition is about 700 mL.

Embodiment P148

The method of any one of Embodiments P123-P146, wherein the volume of the aqueous pharmaceutical composition is about 500 mL to about 900 mL.

Embodiment P149

The method of any one of Embodiments P123-P146, wherein the volume of the aqueous pharmaceutical composition is about 300 mL to about 1,000 mL.

Embodiment P150

The method of any one of Embodiments P123-P146, wherein the volume of the aqueous pharmaceutical composition is about 100 mL to about 2,000 mL.

Embodiment P151

The method of any one of Embodiments P123-P136, wherein the pharmaceutical composition has a volume of about 600 ml to about 800 ml, and comprises about 6.0 grams to about 9.0 grams tranexamic acid, about 28.0 grams to about 37.0 grams polyethylene glycol having a molecular weight of about 3,350, about 22 grams to about 34 grams of glucose, and about 4 grams to about 10.0 grams of at least one electrolyte.

Embodiment P152

The method of any one of Embodiments P123-P136, wherein the pharmaceutical composition has a volume of about 700 ml, and comprises about 7.5 grams tranexamic acid, about 32.5 grams polyethylene glycol having a molecular weight of about 3,350, about 28 grams of glucose, about 4 grams of sodium sulfate, about 1.2 grams sodium bicarbonate, about 1.0 grams sodium chloride, and about 0.5 grams potassium chloride.

Embodiment P153

The method of any one of Embodiments 123-152, further comprising orally administering to the patient or administering to the patient by lavage a therapeutically effective amount of a second aqueous pharmaceutical composition comprising tranexamic acid.

Embodiment P154

The method of Embodiment P153, wherein the second aqueous pharmaceutical composition comprises tranexamic acid and one or more compounds selected from the group consisting of polyethylene glycol, glucose, and an electrolyte.

Embodiment P155

The method of Embodiment P153, wherein the second aqueous pharmaceutical composition comprises tranexamic acid, polyethylene glycol, and at least one electrolyte.

Embodiment P156

The method of Embodiment P153, wherein the second aqueous pharmaceutical composition comprises tranexamic acid, polyethylene glycol, glucose, and at least one electrolyte.

Embodiment P157

The method of Embodiment P153, wherein the second aqueous pharmaceutical composition comprises tranexamic acid, but does not further comprise (i) polyethylene glycol, (ii) glucose, or (iii) polyethylene glycol and glucose.

Embodiment P158

The method of Embodiment P153, wherein the second aqueous pharmaceutical composition is administered to the peritoneal cavity of the patient.

Embodiment P159

The method of Embodiment P153, wherein the second aqueous pharmaceutical composition is administered to the patient by lavage to the stomach, by lavage to the intestines, or by lavage to the stomach and intestines.

Embodiment P160

The method of Embodiment P153, wherein the second aqueous pharmaceutical composition is administered to the patient during a surgical procedure.

Embodiment P161

The method of Embodiment P153, wherein the second aqueous pharmaceutical composition is orally administered to the patient.

Embodiment P162

A method for treating or preventing ileus in a patient in need thereof comprising administering to the patient a therapeutically effective amount of an aqueous pharmaceutical composition comprising tranexamic acid, polyethylene glycol, and at least one electrolyte.

Embodiment P163

The method of Embodiment P162, wherein the aqueous pharmaceutical composition is administered to the patient prior to a surgical procedure.

Embodiment P164

A method for treating or preventing ileus in a patient in need thereof comprising orally administering to the patient a therapeutically effective amount of an aqueous pharmaceutical composition prior to a surgical procedure to treat or prevent ileus; wherein the aqueous pharmaceutical composition comprises tranexamic acid, polyethylene glycol, and at least one electrolyte.

Embodiment P165

The method of Embodiment P162 or P164, wherein the ileus is post-operative ileus.

Embodiment P166

The method of Embodiment P162 or P164, wherein the method for treating or preventing ileus comprises reducing the severity of ileus, decreasing the duration of ileus, or a combination thereof.

Embodiment P167

The method of Embodiment P162 or P164, wherein the method for treating or preventing ileus comprises reducing a complication caused by ileus or to reduce a co-morbidity caused by ileus in a patient in need thereof.

Embodiment P168

The method of Embodiment P162 or P164, wherein the method for treating or preventing ileus comprises on or more of the following: (i) increasing water consumption in the patient; (ii) increasing food consumption in the patient; (iii) increasing fecal production by the patient; (iv) increasing body weight in the patient; and (v) increasing the activity index of the patient.

Embodiment P169

The method of Embodiment P162 or P164 for preventing ileus.

Embodiment P170

The method of any one of Embodiments P162, P163 and P165-P169, comprising orally administering the composition to the patient.

Embodiment P171

The method of Embodiment P163, P164, or P170, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P172

The method of any one of Embodiments P162, P163 and P165-P169, comprising administering the composition to the patient by lavage.

Embodiment P173

The method of Embodiment P172, comprising administering the composition to the peritoneal cavity of the patient by lavage.

Embodiment P174

The method of Embodiment P172, comprising administering the composition to the stomach, to the intestines, or to the stomach and intestines.

Embodiment P175

The method of Embodiment P172, comprising administering the composition to the patient by lavage during a surgical procedure.

Embodiment P176

The method of any one of Embodiments P162-P175, wherein the pharmaceutical composition comprises about 0.9 wt % to about 1.3 wt % of tranexamic acid, about 4.4 wt % to about 4.8 wt % of polyethylene glycol, and about 0.9 wt % to about 1.0 wt % of at least one electrolyte.

Embodiment P177

The method of any one of Embodiments P162-P175, wherein the pharmaceutical composition comprises about 0.7 wt % to about 1.5 wt % of tranexamic acid, about 4.2 wt % to about 5.0 wt % of polyethylene glycol, and about 0.8 wt % to about 1.1 wt % of at least one electrolyte.

Embodiment P178

The method of any one of Embodiments P162-P175, wherein the pharmaceutical composition comprises about 0.4 wt % to about 1.8 wt % of tranexamic acid, about 3.9 wt % to about 5.3 wt % of polyethylene glycol, and about 0.6 wt % to about 1.3 wt % of at least one electrolyte.

Embodiment P179

The method of any one of Embodiments P162-P178, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P180

The method of any one of Embodiments P162-P178, wherein the polyethylene glycol has an average molecular weight of about 3,350 Daltons.

Embodiment P181

The method of any one of Embodiments P162-P180, wherein the electrolyte is sodium, potassium, calcium, magnesium, chloride, bicarbonate, phosphate, sulfate, or a combination of two or more thereof.

Embodiment P182

The method of any one of Embodiments P162-P180, wherein the electrolyte is sodium, sulfate, bicarbonate, chloride, potassium, or a combination of two or more thereof.

Embodiment P183

The method of any one of Embodiments P162-P180, wherein the electrolyte is sodium sulfate, sodium bicarbonate, sodium chloride, potassium chloride, or a combination of two or more thereof.

Embodiment P184

The method of any one of Embodiments P162-P183, wherein the volume of the aqueous pharmaceutical composition is about 700 mL.

Embodiment P185

The method of any one of Embodiments P162-P183, wherein the volume of the aqueous pharmaceutical composition is about 100 mL to about 2,000 mL; or about 300 mL to about 1,000 mL; or about 500 mL to about 900 mL.

Embodiment P186

The method of any one of Embodiments P162-P184, further comprising orally administering to the patient after the surgical procedure or administering to the patient by lavage a therapeutically effective amount of a second aqueous pharmaceutical composition comprising tranexamic acid.

Embodiment P187

The method of Embodiment P186, wherein the second aqueous pharmaceutical composition comprises tranexamic acid and one or more compounds selected from the group consisting of polyethylene glycol, glucose, and an electrolyte.

Embodiment P188

The method of Embodiment P186, wherein the second aqueous pharmaceutical composition comprises tranexamic acid, polyethylene glycol, and at least one electrolyte.

Embodiment P189

The method of Embodiment P186, wherein the second aqueous pharmaceutical composition comprises tranexamic acid, polyethylene glycol, glucose, and at least one electrolyte.

Embodiment P190

The method of Embodiment P186, wherein the second aqueous pharmaceutical composition comprises tranexamic acid, but does not further comprise (i) polyethylene glycol, (ii) glucose, or (iii) polyethylene glycol and glucose.

Embodiment P191

The method of Embodiment P186, wherein the second aqueous pharmaceutical composition is administered to the peritoneal cavity of the patient.

Embodiment P192

The method of Embodiment P186, wherein the second aqueous pharmaceutical composition is administered to the patient by lavage to the stomach, by lavage to the intestines, or by lavage to the stomach and intestines.

Embodiment P193

The method of Embodiment P186, wherein the second aqueous pharmaceutical composition is administered to the patient during a surgical procedure.

Embodiment P194

The method of Embodiment P186, wherein the aqueous pharmaceutical composition is administered to the patient prior to a surgical procedure.

Embodiment P195

A method for treating or preventing ileus in a patient in need thereof comprising administering to the patient a therapeutically effective amount of an aqueous pharmaceutical composition comprising tranexamic acid, and optionally one or more compounds selected from the group consisting of polyethylene glycol, glucose, and at least one electrolyte.

Embodiment P196

The method of Embodiment P195, wherein the aqueous pharmaceutical composition is administered to the patient prior to a surgical procedure.

Embodiment P197

A method for treating or preventing ileus in a patient in need thereof comprising orally administering to the patient a therapeutically effective amount of an aqueous pharmaceutical composition prior to a surgical procedure to treat or prevent adhesions; wherein the aqueous pharmaceutical composition comprises tranexamic acid, and optionally one or more compounds selected from the group consisting of polyethylene glycol, glucose, and at least one electrolyte.

Embodiment P198

The method of Embodiment P195 or P197, wherein the ileus is post-operative ileus.

Embodiment P199

The method of Embodiment P195 or P197, wherein the method for treating or preventing ileus comprises reducing the severity of ileus, decreasing the duration of ileus, or a combination thereof.

Embodiment P200

The method of Embodiment P195 or P197, wherein the method for treating or preventing ileus comprises reducing a complication caused by ileus or to reduce a co-morbidity caused by ileus in a patient in need thereof.

Embodiment P201

The method of Embodiment P195 or P197, wherein the method for treating or preventing ileus comprises on or more of the following: (i) increasing water consumption in the patient; (ii) increasing food consumption in the patient; (iii) increasing fecal production by the patient; (iv) increasing body weight in the patient; and (v) increasing the activity index of the patient.

Embodiment P202

The method of Embodiment P195 or P197 for preventing ileus.

Embodiment P203

The method of any one of Embodiments P195-P202 for preventing ileus comprising orally administering the pharmaceutical composition.

Embodiment P204

The method of any one of Embodiments P195, P196, and P198-P202, comprising orally administering the composition to the patient.

Embodiment P205

The method of Embodiment P196, P197, P203, or P204, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment P206

The method of any one of Embodiments P195, P196, and P198-P202, comprising administering the composition to the patient by lavage.

Embodiment P207

The method of Embodiment P207, comprising administering the composition to the peritoneal cavity of the patient by lavage.

Embodiment P208

The method of Embodiment P207, comprising administering the composition to the stomach, to the intestines, or to the stomach and intestines.

Embodiment P209

The method of Embodiment P207, comprising administering the composition to the patient by lavage during a surgical procedure.

Embodiment P210

The method of any one of Embodiments P195-P209, wherein the pharmaceutical composition comprises tranexamic acid and polyethylene glycol.

Embodiment P211

The method of any one of Embodiments P195-P209, wherein the pharmaceutical composition comprises tranexamic acid and glucose.

Embodiment P212

The method of any one of Embodiments P195-P209, wherein the pharmaceutical composition comprises tranexamic acid and at least one electrolyte.

Embodiment P213

The method of any one of Embodiments P195-P209, wherein the pharmaceutical composition comprises tranexamic acid, glucose, and at least one electrolyte.

Embodiment P214

The method of any one of Embodiments P195-P209, wherein the pharmaceutical composition comprises tranexamic acid, polyethylene glycol, and at least one electrolyte.

Embodiment P215

The method of any one of Embodiments P195-P210 and P214, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment P216

The method of any one of Embodiments P195-P210 and P214, wherein the polyethylene glycol has an average molecular weight of about 3,350 Daltons.

Embodiment P217

The method of any one of Embodiments P199-P209 and P212-P214, wherein the electrolyte is sodium, potassium, calcium, magnesium, chloride, bicarbonate, phosphate, sulfate, or a combination of two or more thereof.

Embodiment P218

The method of any one of Embodiments P199-P209 and P212-P214, wherein the electrolyte is sodium, sulfate, bicarbonate, chloride, potassium, or a combination of two or more thereof.

Embodiment P219

The method of any one of Embodiments P199-P209 and P212-P214, wherein the electrolyte is sodium sulfate, sodium bicarbonate, sodium chloride, potassium chloride, or a combination of two or more thereof.

Embodiment P220

The method of any one of Embodiments P195-P219, wherein the volume of the aqueous pharmaceutical composition is about 700 mL.

Embodiment P221

The method of any one of Embodiments P195-P219, wherein the volume of the aqueous pharmaceutical composition is about 100 mL to about 2,000 mL; or about 300 mL to about 1,000 mL; or about 500 mL to about 900 mL.

Embodiment P222

The method of any one of Embodiments P195-P218, further comprising orally administering to the patient after a surgical procedure or administering to the patient by lavage a therapeutically effective amount of a second aqueous pharmaceutical composition comprising tranexamic acid.

Embodiment P223

The method of Embodiment P222, wherein the second aqueous pharmaceutical composition comprises tranexamic acid and one or more compounds selected from the group consisting of polyethylene glycol, glucose, and an electrolyte.

Embodiment P224

The method of Embodiment P222, wherein the second aqueous pharmaceutical composition comprises tranexamic acid, polyethylene glycol, and at least one electrolyte.

Embodiment P225

The method of Embodiment P222, wherein the second aqueous pharmaceutical composition comprises tranexamic acid, polyethylene glycol, glucose, and at least one electrolyte.

Embodiment P226

The method of Embodiment P222, wherein the second aqueous pharmaceutical composition comprises tranexamic acid, but does not further comprise (i) polyethylene glycol, (ii) glucose, or (iii) polyethylene glycol and glucose.

Embodiment P227

The method of Embodiment P222, wherein the second aqueous pharmaceutical composition is administered to the peritoneal cavity of the patient.

Embodiment P228

The method of Embodiment P222, wherein the second aqueous pharmaceutical composition is administered to the patient by lavage to the stomach, by lavage to the intestines, or by lavage to the stomach and intestines.

Embodiment P229

The method of Embodiment P222, wherein the second aqueous pharmaceutical composition is administered to the patient by lavage during a surgical procedure.

Embodiment P230

The method of Embodiment P222, comprising orally administering the second aqueous pharmaceutical composition to the patient after the surgical procedure.

Embodiment P231

The method of any one of Embodiments P1 to P122 for treating adhesions.

Embodiment P232

The method of any one of Embodiments P1 to P122 for preventing adhesions.

Embodiment P233

The method of any one of Embodiments P123 to P314 for treating ileus.

Embodiment P234

The method of any one of Embodiments P123 to P314 for preventing ileus.

Embodiment 1

A method for treating or preventing adhesions or ileus in a patient in need thereof comprising administering to the patient a therapeutically effective amount of an aqueous pharmaceutical composition comprising tranexamic acid, polyethylene glycol, glucose, and at least one electrolyte.

Embodiment 2

The method of Embodiment 1, wherein the aqueous pharmaceutical composition is administered to the patient prior to a surgical procedure.

Embodiment 3

A method for treating or preventing adhesions or ileus in a patient in need thereof comprising orally administering to the patient a therapeutically effective amount of an aqueous pharmaceutical composition prior to a surgical procedure to treat or prevent adhesions or ileus; wherein the aqueous pharmaceutical composition comprises tranexamic acid, polyethylene glycol, glucose, and at least one electrolyte.

Embodiment 4

The method of Embodiment 1 or 3, wherein the adhesions are surgical adhesions.

Embodiment 5

The method of Embodiment 1 or 3, wherein the adhesions are abdominal adhesions.

Embodiment 6

The method of Embodiment 1 or 3, wherein the adhesions are intestinal adhesions.

Embodiment 7

The method of Embodiment 1 or 3, wherein the adhesions are peritoneal adhesions.

Embodiment 8

The method of Embodiment 1 or 3, wherein the adhesions are intercostal adhesions.

Embodiment 9

The method of Embodiment 1 or 3, wherein the adhesions are abdominal adhesions, intestinal adhesions, peritoneal adhesions, or a combination of two or more thereof.

Embodiment 10

The method of any one of Embodiments 1 to 9, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment 11

The method of any one of Embodiments 1 to 10, wherein treating or preventing adhesions comprises reducing the number of adhesions, reducing the severity of adhesions, or a combination thereof.

Embodiment 12

The method of any one of Embodiments 1 to 9, wherein treating or preventing adhesions or ileus comprises reducing a complication caused by adhesions or ileus, or reducing a co-morbidity caused by adhesions or ileus.

Embodiment 13

The method of Embodiment 12, wherein the complication caused by adhesions or ileus is delayed bowel function recovery, an intestinal obstruction, infertility, pain, or a combination of two or more thereof.

Embodiment 14

The method of any one of Embodiments 1, 2 and 4-13, comprising orally administering the composition to the patient.

Embodiment 15

The method of Embodiment 2, 3 or 14, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment 16

The method of any one of Embodiments 1, 2 and 4-13, comprising administering the composition to the patient by lavage.

Embodiment 17

The method of Embodiment 16, comprising administering the composition to the peritoneal cavity of the patient by lavage.

Embodiment 18

The method of Embodiment 16, comprising administering the composition to an intercostal space in the patient.

Embodiment 19

The method of Embodiment 16, comprising administering the composition to the stomach, to the intestines, or to the stomach and intestines.

Embodiment 20

The method of Embodiment 16, comprising administering the composition to the patient by lavage during a surgical procedure.

Embodiment 21

The method of any one of Embodiments 1-20, wherein the pharmaceutical composition comprises about 1.1 wt % of tranexamic acid, about 4.6 wt % of polyethylene glycol, about 4.0 wt % of glucose, and about 0.96 wt % of at least one electrolyte.

Embodiment 22

The method of any one of Embodiments 1-20, wherein the pharmaceutical composition comprises about 1.1 wt % of tranexamic acid, about 4.6 wt % of polyethylene glycol having an average molecular weight of about 3,350, about 4.0 wt % of glucose, about 0.57 wt % of sodium sulfate, about 0.17 wt % of sodium bicarbonate, about 0.15 wt % of sodium chloride, and about 0.07 wt % of potassium chloride.

Embodiment 23

The method of any one of Embodiments 1-20, wherein the pharmaceutical composition comprises about 0.9 wt % to about 1.3 wt % of tranexamic acid, about 4.4 wt % to about 4.8 wt % of polyethylene glycol, about 3.0 wt % to about 5.0 wt % of glucose, and about 0.9 wt % to about 1.0 wt % of at least one electrolyte.

Embodiment 24

The method of any one of Embodiments 1-20, wherein the pharmaceutical composition comprises about 0.7 wt % to about 1.5 wt % of tranexamic acid, about 4.2 wt % to about 5.0 wt % of polyethylene glycol, about 2.0 wt % to about 6.0 wt % of glucose, and about 0.8 wt % to about 1.1 wt % of at least one electrolyte.

Embodiment 25

The method of any one of Embodiments 1-20, wherein the pharmaceutical composition comprises about 0.4 wt % to about 1.8 wt % of tranexamic acid, about 3.9 wt % to about 5.3 wt % of polyethylene glycol, about 1.0 wt % to about 7.0 wt % of glucose, and about 0.6 wt % to about 1.3 wt % of at least one electrolyte.

Embodiment 26

The method of any one of Embodiments 1-21 and 23-25, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment 27

The method of any one of Embodiments 1-21 and 23-25, wherein the polyethylene glycol has an average molecular weight of about 3,350 Daltons.

Embodiment 28

The method of any one of Embodiments 1-21 and 23-27, wherein the electrolyte is sodium, potassium, calcium, magnesium, chloride, bicarbonate, phosphate, sulfate, or a combination of two or more thereof.

Embodiment 29

The method of any one of Embodiments 1-21 and 23-27, wherein the electrolyte is sodium, sulfate, bicarbonate, chloride, potassium, or a combination of two or more thereof.

Embodiment 30

The method of any one of Embodiments 1-21 and 23-27, wherein the electrolyte is sodium sulfate, sodium bicarbonate, sodium chloride, potassium chloride, or a combination of two or more thereof.

Embodiment 31

The method of any one of Embodiments 1-30, wherein the volume of the aqueous pharmaceutical composition is about 700 mL.

Embodiment 32

The method of any one of Embodiments 1-30, wherein the volume of the aqueous pharmaceutical composition is about 500 mL to about 900 mL.

Embodiment 33

The method of any one of Embodiments 1-30, wherein the volume of the aqueous pharmaceutical composition is about 300 mL to about 1,000 mL.

Embodiment 34

The method of any one of Embodiments 1-30, wherein the volume of the aqueous pharmaceutical composition is about 100 mL to about 2,000 mL.

Embodiment 35

The method of any one of Embodiments 1-20, wherein the pharmaceutical composition has a volume of about 600 ml to about 800 ml, and comprises about 6.0 grams to about 9.0 grams tranexamic acid, about 28.0 grams to about 37.0 grams polyethylene glycol having a molecular weight of about 3,350, about 22 grams to about 34 grams of glucose, and about 4 grams to about 10.0 grams of at least one electrolyte.

Embodiment 36

The method of any one of Embodiments 1-20, wherein the pharmaceutical composition has a volume of about 700 ml, and comprises about 7.5 grams tranexamic acid, about 32.5 grams polyethylene glycol having a molecular weight of about 3,350, about 28 grams of glucose, about 4 grams of sodium sulfate, about 1.2 grams sodium bicarbonate, about 1.0 grams sodium chloride, and about 0.5 grams potassium chloride.

Embodiment 37

The method of any one of Embodiments 1-36, further comprising orally administering to the patient or administering to the patient by lavage a therapeutically effective amount of a second aqueous pharmaceutical composition comprising tranexamic acid.

Embodiment 38

The method of Embodiment 37, wherein the second aqueous pharmaceutical composition comprises tranexamic acid and one or more compounds selected from the group consisting of polyethylene glycol, glucose, and an electrolyte.

Embodiment 39

The method of Embodiment 37, wherein the second aqueous pharmaceutical composition comprises tranexamic acid, polyethylene glycol, and at least one electrolyte.

Embodiment 40

The method of Embodiment 37, wherein the second aqueous pharmaceutical composition comprises tranexamic acid, polyethylene glycol, glucose, and at least one electrolyte.

Embodiment 41

The method of Embodiment 37, wherein the second aqueous pharmaceutical composition comprises tranexamic acid, but does not further comprise (i) polyethylene glycol, (ii) glucose, or (iii) polyethylene glycol and glucose.

Embodiment 42

The method of Embodiment 37, wherein the second aqueous pharmaceutical composition is administered to the peritoneal cavity of the patient.

Embodiment 43

The method of Embodiment 37, wherein the second aqueous pharmaceutical composition is administered to the patient by lavage to the stomach, by lavage to the intestines, or by lavage to the stomach and intestines.

Embodiment 44

The method of Embodiment 37, wherein the second aqueous pharmaceutical composition is administered to an intercostal space of the patient.

Embodiment 45

The method of Embodiments 37, wherein the second aqueous pharmaceutical composition is administered to the patient by lavage during a surgical procedure.

Embodiment 46

The method of Embodiment 37, wherein the second aqueous pharmaceutical composition is orally administered to the patient.

Embodiment 47

A method for treating or preventing adhesions or ileus in a patient in need thereof comprising administering to the patient a therapeutically effective amount of an aqueous pharmaceutical composition comprising tranexamic acid, polyethylene glycol, and at least one electrolyte.

Embodiment 48

The method of Embodiment 47, wherein the aqueous pharmaceutical composition is administered to the patient prior to a surgical procedure.

Embodiment 49

A method for treating or preventing adhesions or ileus in a patient in need thereof comprising orally administering to the patient a therapeutically effective amount of an aqueous pharmaceutical composition prior to a surgical procedure to treat or prevent adhesions or ileus; wherein the aqueous pharmaceutical composition comprises tranexamic acid, polyethylene glycol, and at least one electrolyte.

Embodiment 50

The method of Embodiment 47 or 49, wherein the adhesions are surgical adhesions.

Embodiment 51

The method of Embodiment 47 or 49, wherein the adhesions are abdominal adhesions.

Embodiment 52

The method of Embodiment 47 or 49, wherein the adhesions are intestinal adhesions.

Embodiment 53

The method of Embodiment 47 or 49, wherein the adhesions are peritoneal adhesions.

Embodiment 54

The method of Embodiment 47 or 49, wherein the adhesions are intercostal adhesions.

Embodiment 55

The method of Embodiment 47 or 49, wherein the adhesions are abdominal adhesions, intestinal adhesions, peritoneal adhesions, or a combination of two or more thereof.

Embodiment 56

The method of Embodiment 47 or 49, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment 57

The method of Embodiment 47 or 49, wherein treating or preventing adhesions comprises reducing the number of adhesions, reducing the severity of adhesions, or a combination thereof.

Embodiment 58

The method of Embodiment 47 or 49, wherein treating or preventing adhesions or ileus comprises reducing a complication caused by adhesions or ileus, or reducing a co-morbidity caused by adhesions or ileus.

Embodiment 59

The method of Embodiment 58, wherein the complication caused by adhesions is delayed bowel function recovery, an intestinal obstruction, infertility, pain, or a combination of two or more thereof.

Embodiment 60

The method of any one of Embodiments 47, 48, and 50-59, comprising orally administering the composition to the patient.

Embodiment 61

The method of Embodiment 48, 49, or 60, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment 62

The method of any one of Embodiments 47, 48, and 49-59, comprising administering the composition to the patient by lavage.

Embodiment 63

The method of Embodiment 62, comprising administering the composition to the peritoneal cavity of the patient by lavage.

Embodiment 64

The method of Embodiment 62, comprising administering the composition to an intercostal space in the patient.

Embodiment 65

The method of Embodiment 62, comprising administering the composition to the stomach, to the intestines, or to the stomach and intestines.

Embodiment 66

The method of Embodiment 62, comprising administering the composition to the patient by lavage during a surgical procedure.

Embodiment 67

The method of any one of Embodiments 47-66, wherein the pharmaceutical composition comprises about 0.9 wt % to about 1.3 wt % of tranexamic acid, about 4.4 wt % to about 4.8 wt % of polyethylene glycol, and about 0.9 wt % to about 1.0 wt % of at least one electrolyte.

Embodiment 68

The method of any one of Embodiments 47-66, wherein the pharmaceutical composition comprises about 0.7 wt % to about 1.5 wt % of tranexamic acid, about 4.2 wt % to about 5.0 wt % of polyethylene glycol, and about 0.8 wt % to about 1.1 wt % of at least one electrolyte.

Embodiment 69

The method of any one of Embodiments 47-66, wherein the pharmaceutical composition comprises about 0.4 wt % to about 1.8 wt % of tranexamic acid, about 3.9 wt % to about 5.3 wt % of polyethylene glycol, and about 0.6 wt % to about 1.3 wt % of at least one electrolyte.

Embodiment 70

The method of Embodiment 47, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment 71

The method of any one of Embodiments 47-66, wherein the polyethylene glycol has an average molecular weight of about 3,350 Daltons.

Embodiment 72

The method of any one of Embodiments 47-71, wherein the electrolyte is sodium, potassium, calcium, magnesium, chloride, bicarbonate, phosphate, sulfate, or a combination of two or more thereof.

Embodiment 73

The method of any one of Embodiments 47-71, wherein the electrolyte is sodium, sulfate, bicarbonate, chloride, potassium, or a combination of two or more thereof.

Embodiment 74

The method of any one of Embodiments 47-71, wherein the electrolyte is sodium sulfate, sodium bicarbonate, sodium chloride, potassium chloride, or a combination of two or more thereof.

Embodiment 75

The method of any one of Embodiments 47-74, wherein the volume of the aqueous pharmaceutical composition is about 700 mL.

Embodiment 76

The method of any one of Embodiments 47-74, wherein the volume of the aqueous pharmaceutical composition is about 500 mL to about 900 mL; or about 300 mL to about 1,000 mL; or about 100 mL to about 2,000 mL.

Embodiment 77

The method of any one of Embodiments 47-76, further comprising orally administering to the patient after the surgical procedure or administering to the patient by lavage a therapeutically effective amount of a second aqueous pharmaceutical composition comprising tranexamic acid.

Embodiment 78

The method of Embodiment 77, wherein the second aqueous pharmaceutical composition comprises tranexamic acid and one or more compounds selected from the group consisting of polyethylene glycol, glucose, and an electrolyte.

Embodiment 79

The method of Embodiment 77, wherein the second aqueous pharmaceutical composition comprises tranexamic acid, polyethylene glycol, and at least one electrolyte.

Embodiment 80

The method of Embodiment 77, wherein the second aqueous pharmaceutical composition comprises tranexamic acid, polyethylene glycol, glucose, and at least one electrolyte.

Embodiment 81

The method of Embodiment 77, wherein the second aqueous pharmaceutical composition comprises tranexamic acid, but does not further comprise (i) polyethylene glycol, (ii) glucose, or (iii) polyethylene glycol and glucose.

Embodiment 82

The method of any one of Embodiments 77, wherein the second aqueous pharmaceutical composition is administered to the peritoneal cavity of the patient.

Embodiment 83

The method of any one of Embodiments 77, wherein the second aqueous pharmaceutical composition is administered to the patient by lavage to the stomach, by lavage to the intestines, or by lavage to the stomach and intestines.

Embodiment 84

The method of any one of Embodiments 77, wherein the second aqueous pharmaceutical composition is administered to an intercostal space of the patient.

Embodiment 85

The method of any one of Embodiments 77, wherein the second aqueous pharmaceutical composition is administered to the patient by lavage during a surgical procedure.

Embodiment 86

The method of Embodiment 77, wherein the second aqueous pharmaceutical composition is orally administered to the patient after the surgical procedure.

Embodiment 87

A method for treating or preventing adhesions or ileus in a patient in need thereof comprising administering to the patient a therapeutically effective amount of an aqueous pharmaceutical composition comprising tranexamic acid, and optionally one or more compounds selected from the group consisting of polyethylene glycol, glucose, and at least one electrolyte.

Embodiment 88

The method of Embodiment 87, wherein the aqueous pharmaceutical composition is administered to the patient prior to a surgical procedure.

Embodiment 89

A method for treating or preventing adhesions or ileus in a patient in need thereof comprising orally administering to the patient a therapeutically effective amount of an aqueous pharmaceutical composition prior to a surgical procedure to treat or prevent adhesions or ileus; wherein the aqueous pharmaceutical composition comprises tranexamic acid, and optionally one or more compounds selected from the group consisting of polyethylene glycol, glucose, and at least one electrolyte.

Embodiment 90

The method of Embodiment 87 or 89, wherein the adhesions are surgical adhesions, abdominal adhesions, intestinal adhesions, peritoneal adhesions, intercostal adhesions, or a combination of two or more thereof.

Embodiment 91

The method of Embodiment 87 or 89, wherein the adhesions are abdominal adhesions, intestinal adhesions, peritoneal adhesions, or a combination of two or more thereof.

Embodiment 92

The method of Embodiment 87, wherein treating or preventing adhesions comprises: (i) reducing the incidence of adhesions; (ii) reducing the number of adhesions; (iii) reducing the severity of adhesions; (iv) reducing the thickness of adhesions; (v) reducing the size of the adhesions; (vi) preventing the formation of adhesions; or (vii) a combination of two or more of (i), (ii), (iii), (iv), (v), and (vi).

Embodiment 93

The method of Embodiment 87 or 89, wherein treating or preventing adhesions comprises reducing the number of adhesions, reducing the severity of adhesions, or a combination thereof.

Embodiment 94

The method of Embodiment 87 or 89, wherein treating or preventing adhesions or ileus comprises reducing a complication caused by adhesions or ileus, or reducing a co-morbidity caused by adhesions or ileus.

Embodiment 95

The method of Embodiment 94, wherein the complication caused by adhesions is delayed bowel function recovery, an intestinal obstruction, infertility, pain, or a combination of two or more thereof.

Embodiment 96

The method of any one of Embodiments 87, 88, and 90-95, comprising orally administering the composition to the patient.

Embodiment 97

The method of Embodiment 88, 89, or 96, comprising orally administering a first dose of about 300 ml to about 400 ml of the aqueous pharmaceutical composition about 6 hours to about 8 hours prior to the surgical procedure, and orally administering a second dose of about 300 ml to about 400 ml about 2 hours to about 5 minutes prior to the surgical procedure.

Embodiment 98

The method of any one of Embodiments 87, 88, or 90-95, comprising administering the composition to the patient by lavage.

Embodiment 99

The method of Embodiment 98, comprising administering the composition to the peritoneal cavity of the patient by lavage.

Embodiment 100

The method of Embodiment 98, comprising administering the composition to the stomach, to the intestines, or to the stomach and intestines.

Embodiment 101

The method of Embodiment 98, comprising administering the composition to the patient by lavage during a surgical procedure.

Embodiment 102

The method of any one of Embodiments 87-101, wherein the pharmaceutical composition comprises tranexamic acid and polyethylene glycol.

Embodiment 103

The method of any one of Embodiments 87-101, wherein the pharmaceutical composition comprises tranexamic acid and glucose.

Embodiment 104

The method of any one of Embodiments 87-101, wherein the pharmaceutical composition comprises tranexamic acid and at least one electrolyte.

Embodiment 105

The method of any one of Embodiments 87-101, wherein the pharmaceutical composition comprises tranexamic acid, glucose, and at least one electrolyte.

Embodiment 106

The method of any one of Embodiments 87-101, wherein the pharmaceutical composition comprises tranexamic acid, polyethylene glycol, and at least one electrolyte.

Embodiment 107

The method of any one of Embodiments 87-102 and 106, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

Embodiment 108

The method of any one of Embodiment 87-102 and 106, wherein the polyethylene glycol has an average molecular weight of about 3,350 Daltons.

Embodiment 109

The method of any one of Embodiments 87-101 and 104-106, wherein the electrolyte is sodium, potassium, calcium, magnesium, chloride, bicarbonate, phosphate, sulfate, or a combination of two or more thereof.

Embodiment 110

The method of any one of Embodiments 87-101 and 104-106, wherein the electrolyte is sodium, sulfate, bicarbonate, chloride, potassium, or a combination of two or more thereof.

Embodiment 111

The method of any one of Embodiments 87-101 and 104-106, wherein the electrolyte is sodium sulfate, sodium bicarbonate, sodium chloride, potassium chloride, or a combination of two or more thereof.

Embodiment 112

The method of any one of Embodiments 87-111, wherein the volume of the aqueous pharmaceutical composition is about 700 mL.

Embodiment 113

The method of any one of Embodiments 87-111, wherein the volume of the aqueous pharmaceutical composition is about 100 mL to about 2,000 mL; or about 300 mL to about 1,000 mL; or about 500 mL to about 900 mL.

Embodiment 114

The method of any one of Embodiments 87-113, further comprising orally administering to the patient after a surgical procedure or administering to the patient by lavage a therapeutically effective amount of a second aqueous pharmaceutical composition comprising tranexamic acid.

Embodiment 115

The method of Embodiment 114, wherein the second aqueous pharmaceutical composition comprises tranexamic acid and one or more compounds selected from the group consisting of polyethylene glycol, glucose, and an electrolyte.

Embodiment 116

The method of Embodiment 114, wherein the second aqueous pharmaceutical composition comprises tranexamic acid, polyethylene glycol, and at least one electrolyte.

Embodiment 117

The method of Embodiment 114, wherein the second aqueous pharmaceutical composition comprises tranexamic acid, polyethylene glycol, glucose, and at least one electrolyte.

Embodiment 118

The method of Embodiment 114, wherein the second aqueous pharmaceutical composition comprises tranexamic acid, but does not further comprise (i) polyethylene glycol, (ii) glucose, or (iii) polyethylene glycol and glucose.

Embodiment 119

The method of Embodiment 114, wherein the second aqueous pharmaceutical composition is administered to the peritoneal cavity of the patient.

Embodiment 120

The method of Embodiment 114, wherein the second aqueous pharmaceutical composition is administered to the patient by lavage to the stomach, by lavage to the intestines, or by lavage to the stomach and intestines.

Embodiment 121

The method of Embodiment 114, wherein the second aqueous pharmaceutical composition is administered to the patient by lavage during a surgical procedure.

Embodiment 122

The method of Embodiment 114, comprising orally administering the second aqueous pharmaceutical composition to the patient after the surgical procedure.

Embodiment 123

The method of any one of Embodiments 1, 3, 47, 49, 87, or 89, wherein the ileus is post-operative ileus.

Embodiment 124

The method of any one of Embodiments 1, 3, 47, 49, 87, or 89, wherein the method for treating or preventing ileus comprises reducing the severity of ileus, decreasing the duration of ileus, or a combination thereof.

Embodiment 125

The method of any one of Embodiments 1, 3, 47, 49, 87, or 89, wherein the method for treating or preventing ileus comprises on or more of the following: (i) increasing water consumption in the patient; (ii) increasing food consumption in the patient; (iii) increasing fecal production by the patient; (iv) increasing body weight in the patient; and (v) increasing the activity index of the patient.

Embodiment 126

The method of any one of Embodiments 1-125, wherein the method is for preventing ileus.

Embodiment 127

The method of any one of Embodiments 1-125, wherein the method is for treating ileus.

Embodiment 128

The method of any one of Embodiments 1-125, wherein the method is for preventing and treating ileus.

Embodiment 129

The method of any one of Embodiments 1-125, wherein the method is for preventing adhesions.

Embodiment 130

The method of any one of Embodiments 1-125, wherein the method is for treating adhesions.

Embodiment 131

The method of any one of Embodiments 1-125, wherein the method is for preventing and treating adhesions.

EXAMPLES

The following examples are for purposes of illustration and are not intended to limit the spirit or scope of the disclosure or claims.

Example 1

The objective of the current study was to compare the efficacy of enteral saline, enteral Formula A, lavage tranexamic acid (TXA), and enteral Formula A with lavage TXA to prevent abdominal adhesions in a rat model of surgical adhesions.

As shown in Table 1, Formula A includes water, tranexamic acid (TXA), polyethylene glycol having an average molecular weight of about 3,350 (i.e., PEG 3350), glucose, sodium sulfate, sodium bicarbonate, sodium chloride, and potassium chloride.

TABLE 1

| The components that comprise Formula A. | | | |
|---|---|---|---|
| Component | Formula A (in grams) | Formula A (in wt %) | Source |
| Tranexamic acid | 0.043 g | 1.1 wt % | Daiichi Sankyo |
| PEG 3350 | 0.186 g | 4.6 wt % | OTC clinical grade Miralax |
| Sodium Sulfate (Anhydrous) | 0.023 g | 0.57 wt % | Sigma-Aldrich |
| Sodium Bicarbonate | 0.007 g | 0.17 wt % | Sigma-Aldrich |
| Sodium Chloride | 0.006 g | 0.15 wt % | Sigma-Aldrich |
| Potassium Chloride | 0.003 g | 0.07 wt % | Sigma-Aldrich |
| Glucose | 0.160 g | 4.0 wt % | Sigma-Aldrich |
| Water | 3.628 g | 89.34 wt % | Sterile water for injection |
| Total Solution | 4.055 mL | 100 wt % | |

The tests were conducted on Wistar rats from Harlan/Charles River. The sample size included 40 animals in total, with a target weight of 350-400 g (males). The rat was selected as the test model since it is accepted by regulatory authorities as a rodent animal model for toxicity studies, and high quality animals are readily available and a large amount of background pathology data is available in this species. This rat model of abdominal adhesions is a reproducible model that produces consistent adhesion formation. The model reproducibility provides the ability to observe directional proof of concept data within normal experimental conditions.

The animals were allowed to acclimate to the rodent facility for a minimum period of 3 days before the commencement of experiments. On arrival from the suppliers, the animals were allocated to cages on racks. Animals suspected of being diseased were culled from the study. Wherever possible, any individual animal which failed to perform adequately during acclimation was replaced from the same batch. If significant numbers of animals were unsuitable, the entire batch was rejected and a new batch obtained. For individual identification purposes, each animal was identified using a cage number.

All rats were housed in a SPF (specific pathogen free) facility with Innovive disposable cages system. The cage product code: R-BTM-C8 (disposable, pre-bedded with corn cob). The cage dimensions: 42 cm L×34 cm W×19.8 cm H. 4-5 rats can be housed in one cage. Housing was in compliance with the space recommendations of Guide for the Care and Use of Laboratory Animals.

The targeted conditions for animal room environment were as follows: Temperature: 19-23° C.; Humidity: 40-70%; Ventilation: A minimum of 10 air changes per hour; Light Cycle: 12 hours light and 12 hours dark (except when interrupted by study procedures/activities). Automatic control of temperature was continuously monitored and recorded. Humidity was continuously monitored and recorded. Deviations from target temperature and humidity ranges were presented in the study report. There was automatic control of light cycle. Rat diet was from Charles River Laboratories, and provided to all rats in sanitized feeding devices of Innovive cages system, ad libitum. Approximately 12 hours before test article administration, rats were fasted from until the completion of the surgical procedure.

Four groups were measured; Group 1 served as the control wherein saline (Baxter, 0.9% sodium chloride IV solution bags) was administered via enteral administration; subjects in Group 2 were exposed to an enteral administration of Formula A; subjects in Group 3 were exposed to a lavage of tranexamic acid (TXA) and saline; and subjects in Group 4 were given enteral administration of Formula A and a lavage of tranexamic acid (TXA) and saline.

TABLE 2 gives an overview of the experimental design.

| Group No. | N per group | Animal Numbers | Enteral Test Item | Enteral Dose Volume | Lavage Test Item | Lavage Volume | No. of Administrations |
|---|---|---|---|---|---|---|---|
| 1 | 10 | 101-110 | Saline | 4 ml oral gavage 2 hr pre surgery | none | none | 1X |
| 2 | 10 | 201-210 | Formula A | 4 ml oral gavage 2 hr pre surgery | none | none | 1X |
| 3 | 10 | 301-310 | none | N/A | TXA in saline | 4 ml | 1X |
| 4 | 10 | 401-410 | Formula A | 4 ml oral gavage 2 hr pre surgery | TXA in saline | 4 ml | 1X |

Prior to the experiment, the animals were fasted and prepared for the adhesion model according to the schedule: (A) Evening Prior to Experiment—Begin Fasting; (B) Day 1: Hour—2.0—Administration of enteral test article (oral gavage); (C) Day 1: Hour 0.0—Induction of anesthesia with ketamine with a dose of 75 mg/kg, I.M; and (D) Day 1: Hour 0+10 min—induction of surgical adhesion model.

A small skin incision in the midline of the abdomen was made for isolation of small intestine. A length of the small intestine was rubbed gently with a latex glove 10 times. Animals were given abdominal lavage test article immediately after the small intestine was rubbed. Laparotomy was sutured and the animal allowed to recover. During surgery, the animals were kept warm (37° C.) at all times by a temperature therapy pad and vital signs (systemic blood pressure or respiratory rate, body temperature) were monitored at all times during experiment. Leg motion and toe reflexes were monitored for anesthetic level. On day 28—The animals were euthanized and the number and size/thickness of adhesions were quantified.

Figure 2:
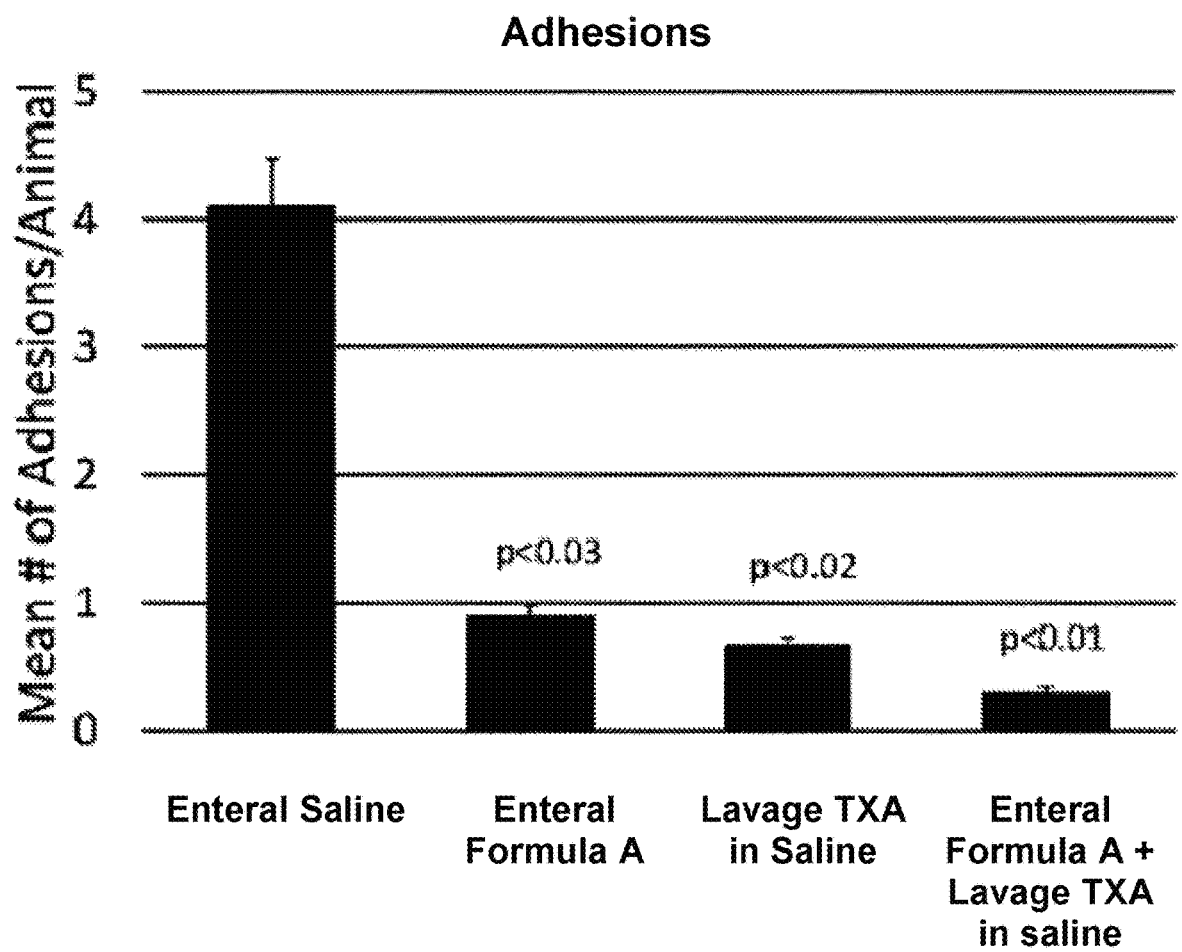
FIG. 2 is a graph showing the mean number of adhesions per animal for each group described in Example 1.

FIG. 2 shows the mean number of adhesions observed in each of Groups 1-4 above. The mean number of adhesions in Group 1 was 4.10. The mean number of adhesions in Group 2 was 0.9. The mean number of adhesions in Group 3 was 0.67. The mean number of adhesions in Group 4 was 0.30. In each of Groups 2, 3, and 4, the mean number of adhesions was significant relative to the control Group 1 as determined by a 2 side T-test. FIG. 2 demonstrates that the groups which received enteral Formula A and a combination of enteral administration of Formula A with a tranexamic acid (TXA) lavage resulted in significantly less adhesions relative to the control.

Figure 3:
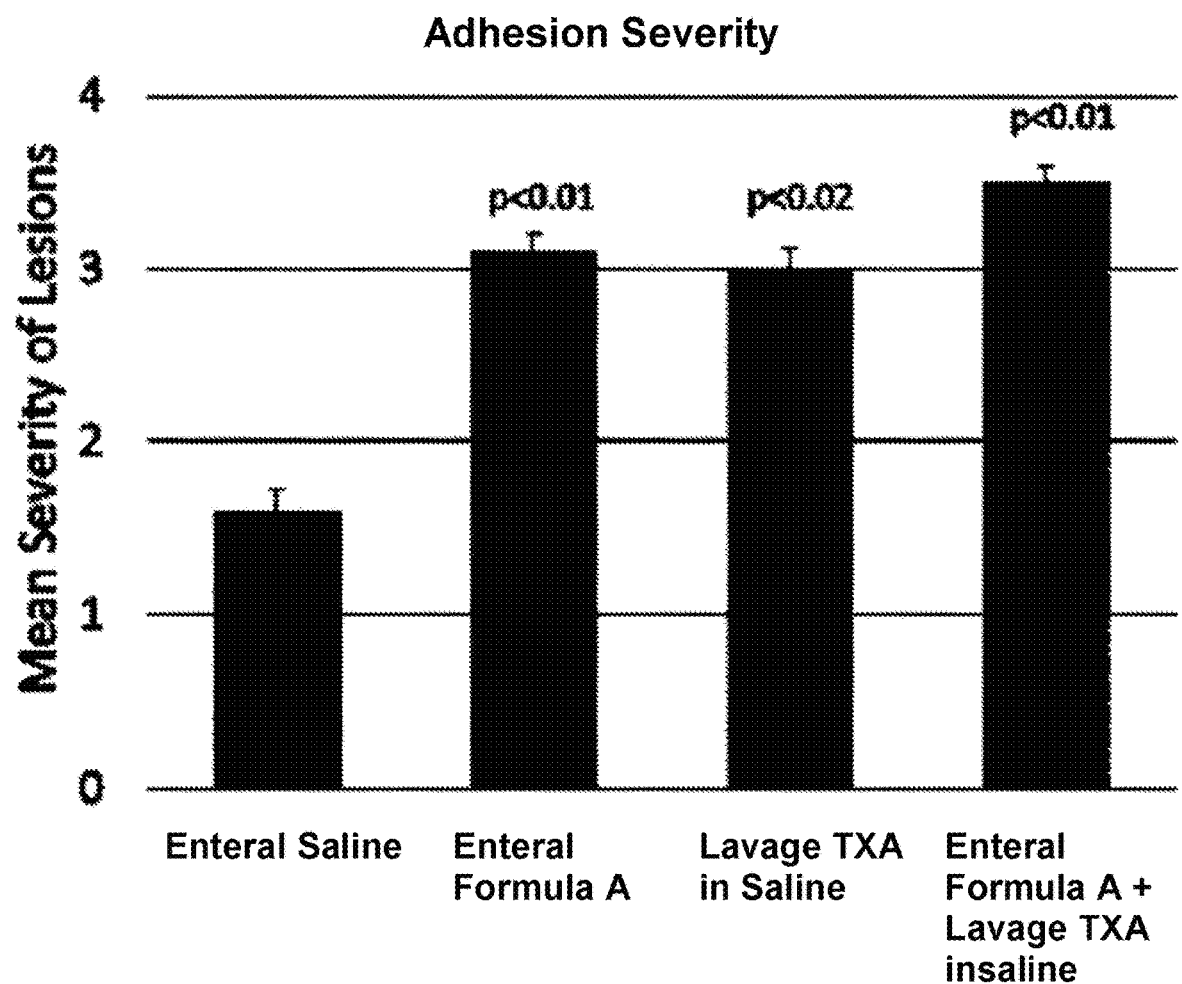
FIG. 3 is a graph showing the mean severity of adhesions per animal for each group described in Example 1.

FIG. 3 shows the mean severity of adhesions observed in each of Groups 1-4 above. Scores were given as follows: a score of 4 is no adhesions detected/measured; a score of 3 is less than 1 mm, or ≤1 mm; a score of 2 is greater than 1 mm but less than 2 mm, or >1 mm≤2 mm; a score of 1 is given as greater than 2 mm, or >2 mm; a score of 0 is given if the adhesion resulted in a kinked intestine. The mean severity of adhesions in Group 1 was 1.60. The mean severity of adhesions in Group 2 was 3.10. The mean severity of adhesions in Group 3 was 3.00. The mean severity of adhesions in Group 4 was 3.50. In each of Groups 2, 3, and 4, the mean severity of adhesions was significant relative to the control Group 1 as determined by a 2 side T-test. FIG. 3 demonstrates that the groups which received enteral Formula A and a combination of enteral administration of Formula A with a tranexamic acid (TXA) lavage resulted in significantly smaller adhesions in terms of thickness/severity relative to the control.

Example 2

This study was conducted with Formula A described in Table 1 (with reference to wt %). The placebo used in this study was an aqueous formulation comprising about 4.6 wt % of polyethylene glycol having an average molecular weight of about 3,350, about 4.0 wt % of glucose, about 0.57 wt % of sodium sulfate, about 0.17 wt % of sodium bicarbonate, about 0.15 wt % of sodium chloride, and about 0.07 wt % of potassium chloride.

24 Wistar rats were randomized and administered either Formula A, saline, or a placebo via an oral gavage 2 hours prior to bowel resection surgery. Following bowel resection surgery, the rats were monitored for 35 days and various biologic measurements were taken. After 35 days, the rats were euthanized, a laparotomy was performed, and adhesions were measured.

Figure 4:
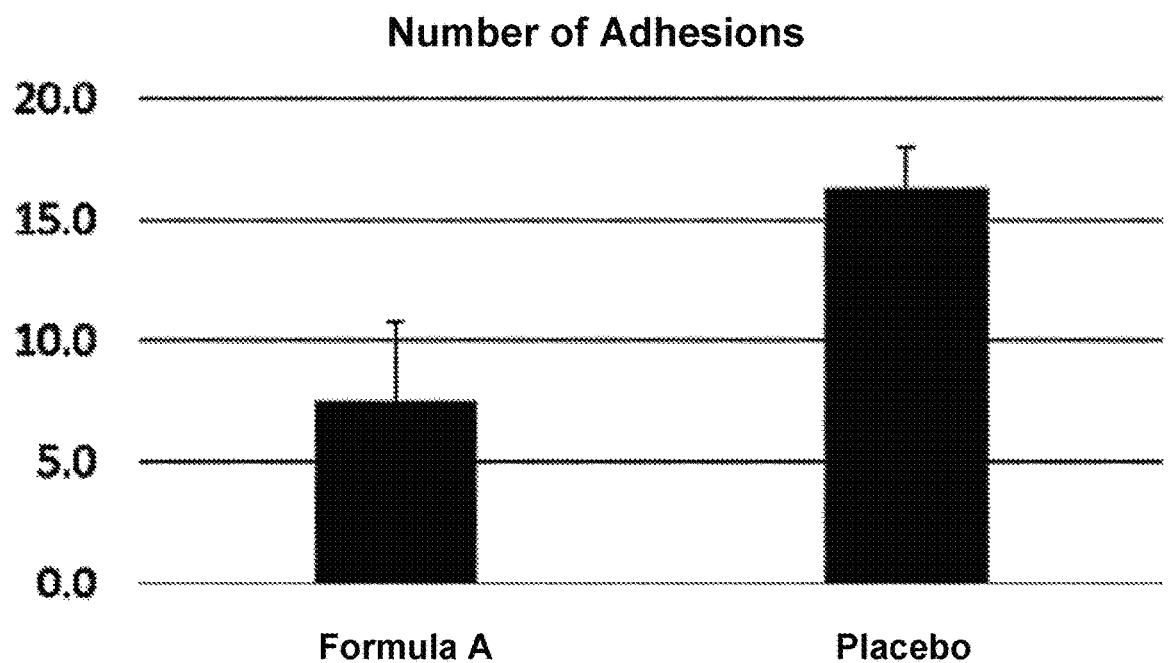
FIG. 4 is a graph showing the average number of adhesions for 16 of the 24 rats described in Example 2.

FIG. 4 shows the average number of adhesions observed in 16 of the rats administered Formula A or placebo. The rats administered Formula A had an average of 7.5 adhesions (standard deviation=6.5; SEM=3.2). The rats administered placebo had an average of 16.3 adhesions (standard deviation=3.5; SEM=2.7). Thus, the rats that were administered Formula A had significantly less adhesions 35 days post-surgery compared to the rats that were administered placebo.

Figure 5:
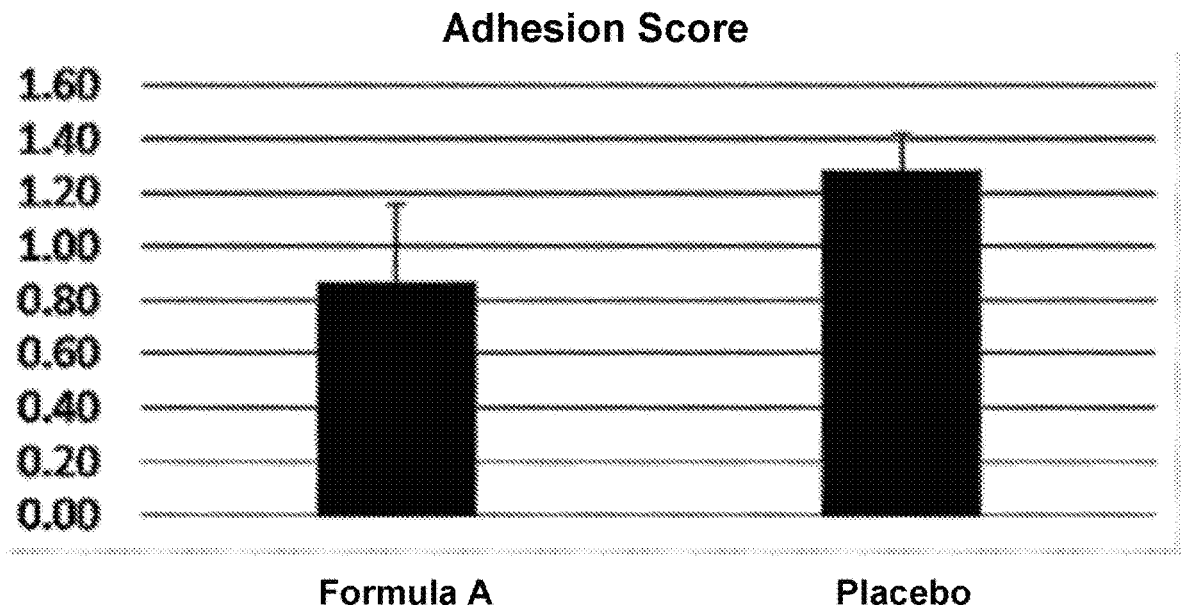
FIG. 5 is a graph showing the average severity of adhesions for 16 of the 24 rats described in Example 2.
Figure 6:
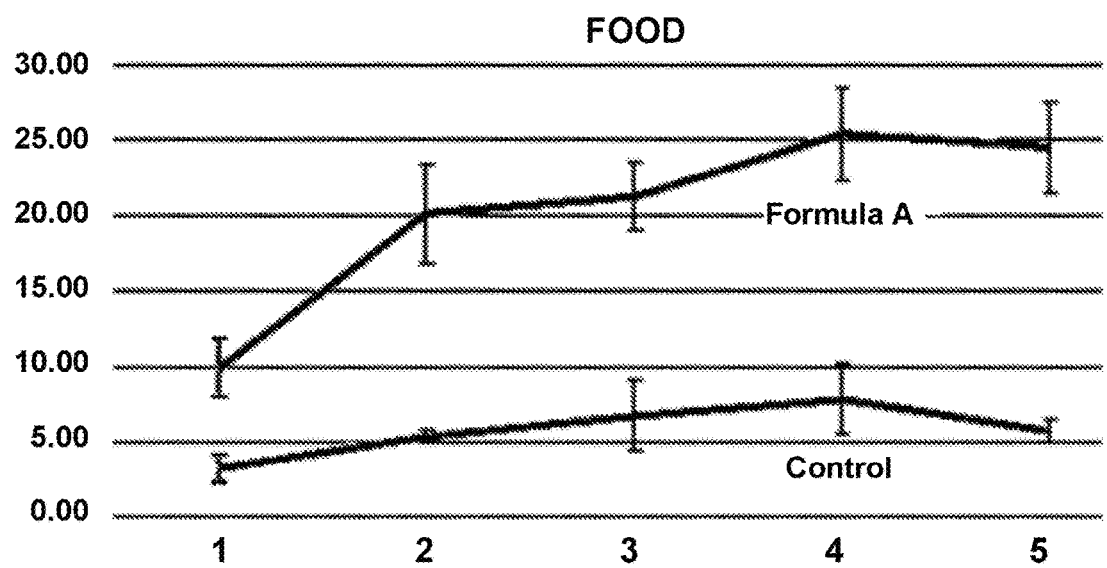
FIG. 6 is a graph showing that rats administered Formula A two hours prior to bowel resection surgery had greater food consumption following surgery when compared to the control, thus demonstrating the efficacy of Formula A in treating and preventing ileus. The x-axis represents Days 1, 2, 3, 4, and 5 following bowel resection surgery. The y-axis represents the number of grams of food eaten.
Figure 7:
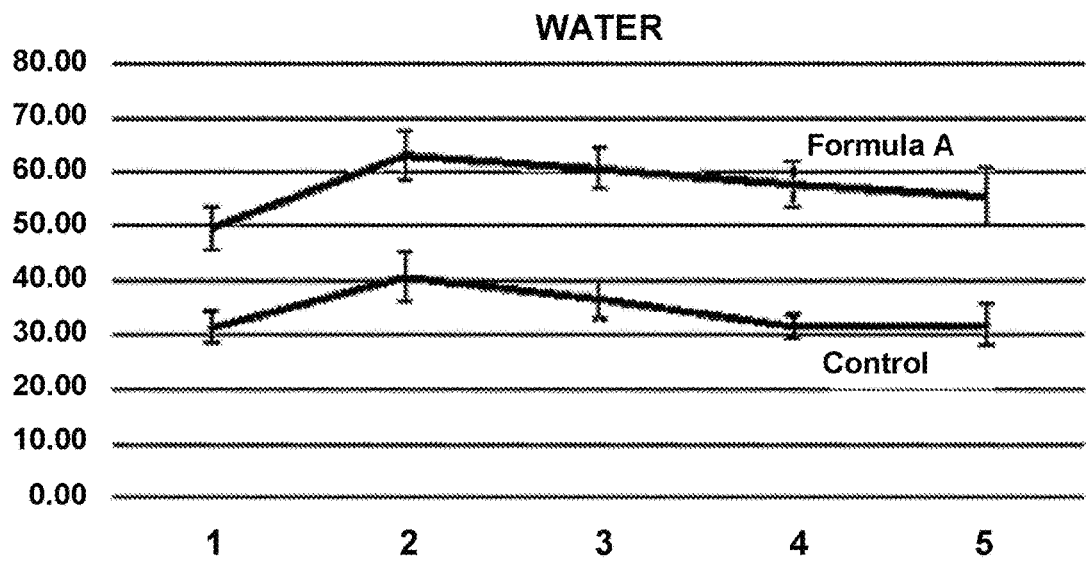
FIG. 7 is a graph showing that rats administered Formula A two hours prior to bowel resection surgery had greater water consumption following surgery when compared to the control, thus demonstrating the efficacy of Formula A in treating and preventing ileus. The x-axis represents Days 1, 2, 3, 4, and 5 following bowel resection surgery. The y-axis represents the number of grams of water the rats drank.
Figure 8:
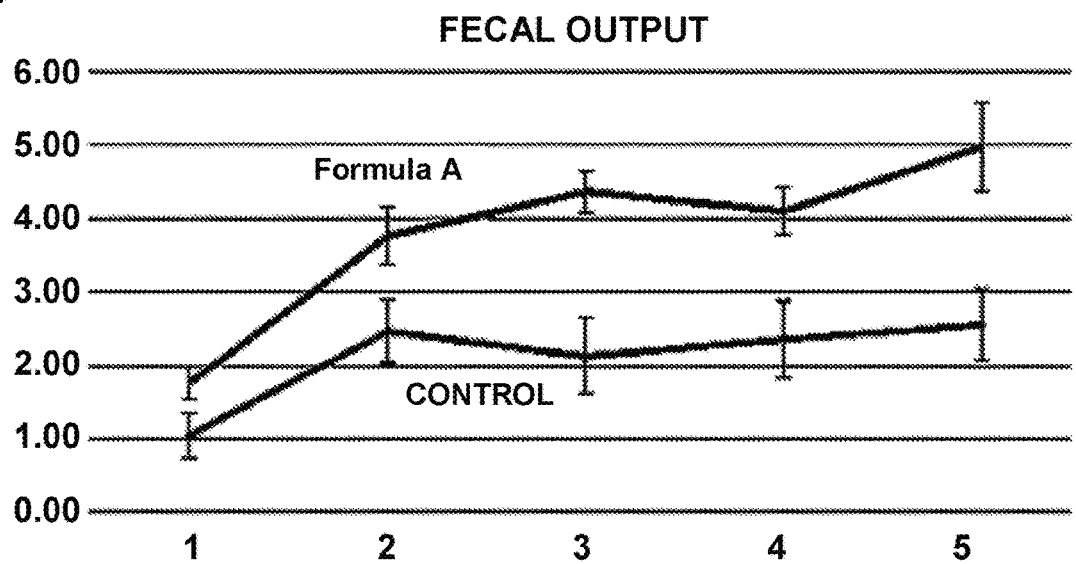
FIG. 8 is a graph showing that rats administered Formula A two hours prior to bowel resection surgery had greater fecal output following surgery when compared to the control, thus demonstrating the efficacy of Formula A in treating and preventing ileus. The x-axis represents Days 1, 2, 3, 4, and 5 following bowel resection surgery. The y-axis represents the number of grams of feces produced by the rats.
Figure 9:
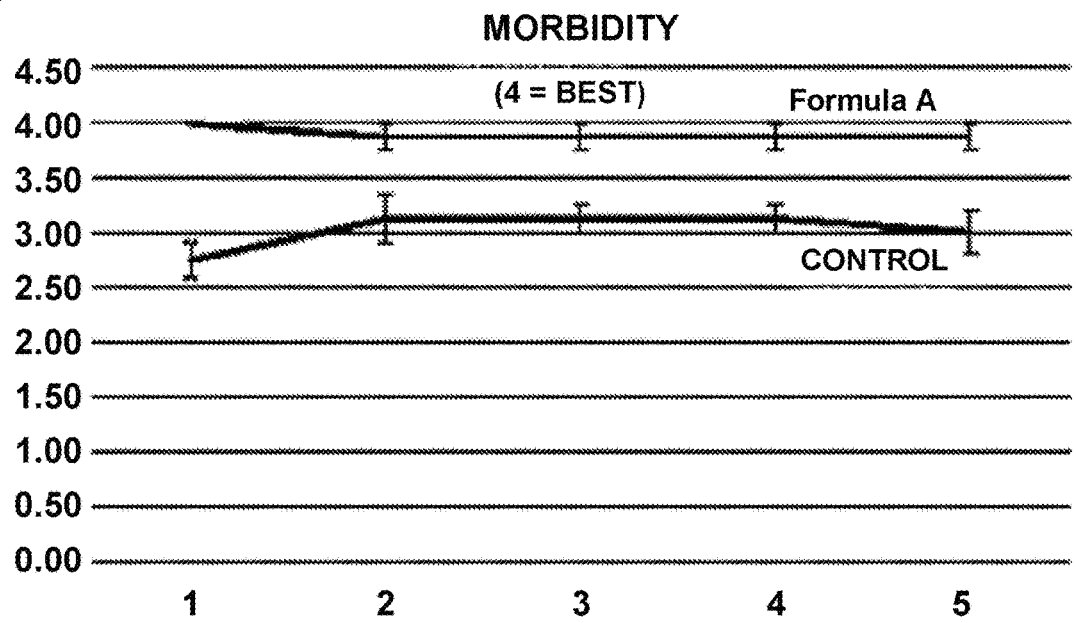
FIG. 9 is a graph showing that rats administered Formula A two hours prior to bowel resection surgery had decreased morbidity following surgery when compared to the control, thus demonstrating the efficacy of Formula A in treating and preventing ileus. The x-axis represents Days 1, 2, 3, 4, and 5 following bowel resection surgery. The y-axis represents an activity level index ranging from 0 to 4 where a score of 4 represents normal rat activity.

FIG. 5 shows the mean severity of adhesions observed in the rats administered Formula A or placebo. Scores were given as follows: a score of 4 is no adhesions detected/measured; a score of 3 is less than 1 mm, or ≤1 mm; a score of 2 is greater than 1 mm but less than 2 mm, or >1 mm≤2 mm; a score of 1 is given as greater than 2 mm, or >2 mm; a score of 0 is given if the adhesion resulted in a kinked intestine. The rats administered Formula A had an average severity score of 0.87 (standard deviation=0.58; SEM=0.29). The rats administered placebo had an average severity score of 1.29 (standard deviation=0.27; SEM=0.13. Thus, the rats that were administered Formula A had similar adhesion severity scores 35 days post-surgery compared to the rats that were administered placebo.

Example 3

During abdominal surgery, surgeons handle, manipulate, and may make incisions in the bowel. These actions create bruising, lesions, and microscopic damage to the bowel, which allows digestive enzymes to cross the mucosal barrier and leak from the bowel. This leak of digestive enzymes during surgery, which is normally not life threatening, may cause local tissue and organ damage. Because of its proximity to the leak, the bowel is one of the most seriously affected organs and the digestive enzyme leak may lead to lack of motility in the intestine, called ileus which results in post-operative ileus. The animal model described in this example replicates such issues in human surgery, and predictive of the results in humans.

This study was conducted with Formula A described in Table 1 above (with reference to wt % of the components). The control used in this study was an aqueous formulation comprising about 4.6 wt % polyethylene glycol having an average molecular weight of about 3,350, about 4.0 wt % glucose, about 0.57 wt % sodium sulfate, about 0.17 wt % sodium bicarbonate, about 0.15 wt % sodium chloride, and about 0.07 wt % potassium chloride.

24 Wistar rats, having a weight of about 400 grams, were randomized and administered 4 mL of either Formula A or control via an oral gavage 2 hours prior to bowel resection surgery. Following bowel resection surgery, the rats were monitored for 7 days and biologic measurements involving post-operative ileus were measured. The measurements included body weight, food consumption, water consumption, fecal production, and morbidity measured by an activity index, based on activity in their home cage. Symptoms of ileus include reduced food and water consumption, reduced fecal production, and reduced activity index.

As shown in FIGS. 5-9, the rats given Formula A had increased food and water consumption, increased fecal production and a higher activity index when compared to the control. All of these results were significant to less than a 0.01 level.

As shown by this example, Formula A stopped the downstream effects of a disruption of the mucosal barrier. A single dose of Formula A helped to stop the leakage, prevent subsequent organ damage, and help heal the intestinal mucosal barrier.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for treating adhesions or ileus in a patient in need thereof, the method comprising orally administering to the patient, prior to a surgical procedure, a therapeutically effective amount of an aqueous pharmaceutical composition comprising tranexamic acid, polyethylene glycol, glucose, and at least one electrolyte.

2. The method of claim 1, wherein the aqueous pharmaceutical composition is orally administered to the patient in two doses prior to a surgical procedure.

3. The method of claim 1, further comprising orally administering to the patient after the surgical procedure or administering to the patient by lavage during the surgical procedure a therapeutically effective amount of a second aqueous pharmaceutical composition comprising tranexamic acid.

4. The method of claim 1, wherein the adhesions are surgical adhesions, abdominal adhesions, intestinal adhesions, peritoneal adhesions, intercostal adhesions, or a combination of two or more thereof.

5. The method of claim 1, wherein the pharmaceutical composition comprises about 0.1 wt % to about 5.0 wt % of tranexamic acid, about 0.1 wt % to about 10 wt % of polyethylene glycol, about 0.1 wt % to about 20.0 wt % of glucose, and about 0.05 wt % to about 10 wt % of at least one electrolyte.

6. The method of claim 1, wherein the pharmaceutical composition comprises 0.1 wt % to about 2.5 wt % of tranexamic acid, about 2.5 wt % to about 8.0 wt % of polyethylene glycol, about 0.1 wt % to about 10.0 wt % of glucose, and about 0.1 wt % to about 2.5 wt % of at least one electrolyte.

7. The method of claim 1, wherein the polyethylene glycol has an average molecular weight from about 100 Daltons to about 10,000 Daltons; or from about 100 Daltons to about 9,000 Daltons; or from about 500 Daltons to about 8,000 Daltons; or from about 1,000 Daltons to about 6,000 Daltons; or from about 2,000 Daltons to about 5,000 Daltons; or from about 2,500 Daltons to about 4,500 Daltons; or from about 3,000 Daltons to about 4,000 Daltons; or from about 3,000 Daltons to about 3,500 Daltons; or from about 3,300 Daltons to about 3,400 Daltons.

8. The method of claim 1, wherein the polyethylene glycol has an average molecular weight of about 3,350 Daltons.

9. The method of claim 1, wherein the electrolyte is sodium, potassium, calcium, magnesium, chloride, bicarbonate, phosphate, sulfate, or a combination of two or more thereof.

10. The method of claim 1, wherein the electrolyte is sodium sulfate, sodium bicarbonate, sodium chloride, potassium chloride, or a combination of two or more thereof.

11. The method of claim 1, wherein the volume of the aqueous pharmaceutical composition is 700 mL; 500 mL to 900 mL; 300 mL to 1,000 mL; or 100 mL to 2,000 mL.

12. The method of claim 1, wherein treating adhesions comprises reducing the number of adhesions; reducing the severity of adhesions; reducing the thickness of adhesions; reducing the size of adhesions; or a combination of two or more thereof.

13. The method of claim 1, wherein treating adhesions comprises reducing the number of adhesions; reducing the severity of adhesions; or a combination thereof.

14. A method for treating adhesions or ileus in a patient in need thereof, the method comprising orally administering to the patient, prior to a surgical procedure, a therapeutically effective amount of an aqueous pharmaceutical composition comprising tranexamic acid, and optionally one or more components selected from the group consisting of polyethylene glycol, glucose, and at least one electrolyte.

15. The method of claim 14, wherein the aqueous pharmaceutical composition is orally administered to the patient in two doses prior to a surgical procedure.

16. The method of claim 14, further comprising orally administering to the patient after the surgical procedure or administering to the patient by lavage during the surgical procedure a therapeutically effective amount of a second aqueous pharmaceutical composition comprising tranexamic acid.

17. The method of claim 14, wherein the adhesions are surgical adhesions, abdominal adhesions, intestinal adhesions, peritoneal adhesions, intercostal adhesions, or a combination of two or more thereof.

18. The method of claim 14, wherein the pharmaceutical composition comprises tranexamic acid and at least one electrolyte.

19. The method of claim 14, wherein treating adhesions comprises reducing the number of adhesions; reducing the severity of adhesions; reducing the thickness of adhesions; reducing the size of adhesions; or a combination of two or more thereof.

20. The method of claim 14, wherein treating adhesions comprises reducing the number of adhesions; reducing the severity of adhesions; or a combination thereof.

\* \* \* \* \*